United States Patent [19]

Murphy

[11] Patent Number: 5,712,118
[45] Date of Patent: *Jan. 27, 1998

[54] VACCINE FOR BRANHAMELLA CATARRHALIS

[75] Inventor: Timothy F. Murphy, East Amherst, N.Y.

[73] Assignee: Research Foundation of State University of New York, Amherst, N.Y.

[*] Notice: The term of this patent shall not extend beyond the expiration date of Pat. No. 5,556,755.

[21] Appl. No.: 306,871

[22] Filed: Sep. 20, 1994

Related U.S. Application Data

[63] Continuation-in-part of Ser. No. 129,719, Sep. 29, 1993, Pat. No. 5,556,755.

[51] Int. Cl.$^6$ ............... C12N 15/00; C12N 7/00; C07K 1/00; C07H 19/00

[52] U.S. Cl. .............. 435/69.3; 435/320.1; 435/252.1; 435/87.1; 435/91.1; 435/91.4 T; 435/235.1; 435/172.3; 536/22.1; 536/23.1; 530/350

[58] Field of Search .................... 435/69.3, 320.1, 435/252.1, 172.3; 536/22.1, 23.1; 530/350

[56] References Cited

U.S. PATENT DOCUMENTS 5,556,755  9/1996  Murphy.

OTHER PUBLICATIONS

Murphy et al. 1993. The major heat-modifiable outer membrane protein CD . . . Mal. Microbiol. 10(1):87–97.
Helminen et al. 1993. A major outer membrane protein of Moraxella catahrhalis . . . 61(5):2003–2010.
Houghten et al. 1986. Vaccines 86. pp. 21–25.
Sarwar et al. 1992. Inf & Imm. 60(3):804–809.

*Primary Examiner*—Paula K. Hutzell
*Assistant Examiner*—N. M. Minnifield
*Attorney, Agent, or Firm*—Hodgson, Russ, Andrews, Woods & Goodyear

[57] ABSTRACT

Compositions comprising outer membrane protein "CD", and peptides and oligopeptides thereof, of *Branhamella catarrhalis* are described. Additionally, nucleotide sequences encoding the protein, peptide or oligopeptide are disclosed, as well as recombinant vectors containing these sequences. Protein, peptide or oligopeptide can be produced from host cell systems containing these recombinant vectors. Peptides and oligopeptides can also be chemically synthesized. Disclosed are the uses of the protein, peptides and oligopeptides as antigens for vaccine formulations, and as antigens in diagnostic immunoassays. The nucleotide sequences are useful for constructing vectors for use as vaccines for insertion into attenuated bacteria in constructing a recombinant bacterial vaccine, and for inserting into a viral vector in constructing a recombinant viral vaccine. Also described is the use of nucleotide sequences related to the gene encoding CD as primers and/or probes in molecular diagnostic assays for the detection of *B. catarrhalis*.

9 Claims, 3 Drawing Sheets

SEQUENCE LISTING ( 1 ) GENERAL INFORMATION:

( i i i ) NUMBER OF SEQUENCES: 52

( 2 ) INFORMATION FOR SEQ ID NO:1:

( i ) SEQUENCE CHARACTERISTICS:
        ( A ) LENGTH: 387 nucleotides
        ( B ) TYPE: nucleic acid
        ( C ) STRANDEDNESS: double-stranded
        ( D ) TOPOLOGY: linear ( i i ) MOLECULE TYPE: genomic DNA ( i i i ) HYPOTHETICAL: yes ( i v ) IMMEDIATE SOURCE:
        ( A ) LIBRARY: genomic
        ( B ) CLONE: lambda gt11 clone ( v ) ORIGINAL SOURCE:
        ( A ) ORGANISM: Branhamella catarrhalis
        ( B ) STRAIN: 25240
        ( C ) CELL TYPE: bacterium ( v i ) FEATURE:
        ( A ) LOCATION: CD gene region, 775- 1160
        ( B ) IDENTIFICATION METHOD: by experiment
        ( C ) OTHER INFORMATION: contains sequence encoding epitopes
            recognized by CD-specific monoclonal antibodies 5E8 and 7D6

( v i i ) SEQUENCE DESCRIPTION: SEQ ID NO: 1:

```
GCT GGT TTA GAG GTA ACT TTG GGT GGT CGT TTG GCA GCT GCA        42
Ala Gly Leu Glu Val Thr Leu Gly Gly Arg Leu Ala Pro Ala
 1               5                   10

GTA CCA GTA GCA CCA GTG GCA GAA CCT GTT GCT GAA CCA GTT        84
Val Pro Val Ala Pro Val Ala Glu Pro Val Ala Glu Pro Val
15                   20                  25

GTT GCT CCA GCA CCT GTG ATC CTT CCT AAA CCA GAA CCT GAG       126
Val Ala Pro Ala Pro Val Ile Leu Pro Lys Pro Glu Pro Glu
         30                  35                  40

CCT GTC ATT GAG GAA GCA CCA GCT GTA ATT GAA GAT ATT GTT       168
Pro Val Ile Glu Glu Ala Pro Ala Val Ile Glu Asp Ile Val
             45                  50                  55

GTT GAT TCA GAC GGA GAT GGT GTG CCT GAT CAT CTG GAT GCC       210
Val Asp Ser Asp Gly Asp Gly Val Pro Asp His Leu Asp Ala
                 60                  65                  70

TGC CCA GGA ACT CCA GTA AAC ACT GTT GTT GAT CCA CGC GGT       252
Cys Pro Gly Thr Pro Val Asn Thr Val Val Asp Pro Arg Gly
                     75                  80

TGC CCA GTA CAG GTT AAT TTG GTA GAA GAG CTT CGC CAA GAG       294
Cys Pro Val Gln Val Asn Leu Val Glu Glu Leu Arg Gln Glu
85                   90                  95

TTG CGT GTA TTC TTT GAT TAT GAT AAA TCA ATC ATC AAA CCA       336
Leu Arg Val Phe Phe Asp Tyr Asp Lys Ser Ile Ile Lys Pro
    100                 105                 110

CAA TAC CGT GAA GAA GTT GCT AAG GTT GCT GCG CAA ATG CGT       378
Gln Tyr Arg Glu Glu Val Ala Lys Val Ala Ala Gln Met Arg
        115                 120                 125

GAA TTC CCA         387
Glu Phe Pro
        129
```

( 2 ) INFORMATION FOR SEQ ID NO:2:

( i ) SEQUENCE CHARACTERISTICS:
        ( A ) LENGTH: 20 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Branhamella catarrhalis
        ( B ) STRAIN: 25240

( i i i ) FEATURE:
        ( A ) LOCATION: CD gene region, 1116- 1135
        ( B ) IDENTIFICATION METHOD: by experiment
        ( C ) OTHER INFORMATION: hybridizes to Branhamella catarrhalis
            gene region ( i v ) SEQUENCE DESCRIPTION: SEQ ID NO: 2:

CCGTGAAGAA GTTGCTAAGG        20

( 2 ) INFORMATION FOR SEQ ID NO:3:

( i ) SEQUENCE CHARACTERISTICS:
        ( A ) LENGTH: 15 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Branhamella catarrhalis
        ( B ) STRAIN: 25240

( i i i ) FEATURE:
        ( A ) LOCATION: CD gene region, 206- 220
        ( B ) IDENTIFICATION METHOD: by experiment
        ( C ) OTHER INFORMATION: hybridizes to Branhamella catarrhalis gene region ( i v ) SEQUENCE DESCRIPTION: SEQ ID NO: 3:

CTGACGAAGT CCACA  15

( 2 ) INFORMATION FOR SEQ ID NO:4:

( i ) SEQUENCE CHARACTERISTICS:
        ( A ) LENGTH: 16 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Branhamella catarrhalis
        ( B ) STRAIN: 25240

( i i i ) FEATURE:
        ( A ) LOCATION: CD gene region (complementary strand), 316-331
        ( B ) IDENTIFICATION METHOD: by experiment
        ( C ) OTHER INFORMATION: hybridizes to Branhamella catarrhalis
        gene region ( i v ) SEQUENCE DESCRIPTION: SEQ ID NO: 4:

CACCAGTCCA TAGCTC  16

( 2 ) INFORMATION FOR SEQ ID NO:5:

( i ) SEQUENCE CHARACTERISTICS:
        ( A ) LENGTH: 16 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Branhamella catarrhalis
        ( B ) STRAIN: 25240

( i i i ) FEATURE:
        ( A ) LOCATION: CD gene region, 468- 483
        ( B ) IDENTIFICATION METHOD: by experiment
        ( C ) OTHER INFORMATION: hybridizes to Branhamella catarrhalis
        gene region ( i v ) SEQUENCE DESCRIPTION: SEQ ID NO: 5:

GATTGGTACT GAGCAG  16

( 2 ) INFORMATION FOR SEQ ID NO:6:

( i ) SEQUENCE CHARACTERISTICS:
        ( A ) LENGTH: 18 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Branhamella catarrhalis
        ( B ) STRAIN: 25240

( i i i ) FEATURE:
        ( A ) LOCATION: CD gene region (complementary strand), 561-578
        ( B ) IDENTIFICATION METHOD: by experiment
        ( C ) OTHER INFORMATION: hybridizes to Branhamella catarrhalis
        gene region ( i v ) SEQUENCE DESCRIPTION: SEQ ID NO: 6:

GTATAACCAT CAATTGCA  18

( 2 ) INFORMATION FOR SEQ ID NO:7:

( i ) SEQUENCE CHARACTERISTICS:
        ( A ) LENGTH: 15 nucleotides (B) TYPE: nucleic acid
                (C) STRANDEDNESS: single-stranded
                (D) TOPOLOGY: linear (ii) ORIGINAL SOURCE:
                (A) ORGANISM: Branhamella catarrhalis
                (B) STRAIN: 25240

(iii) FEATURE:
                (A) LOCATION: CD gene region, 724-738
                (B) IDENTIFICATION METHOD: by experiment
                (C) OTHER INFORMATION: hybridizes to Branhamella catarrhalis gene region (iv) SEQUENCE DESCRIPTION: SEQ ID NO: 7:

GCCCGTGCTA TCCAT    15

(2) INFORMATION FOR SEQ ID NO:8:

(i) SEQUENCE CHARACTERISTICS:
                (A) LENGTH: 17 nucleotides
                (B) TYPE: nucleic acid
                (C) STRANDEDNESS: single-stranded
                (D) TOPOLOGY: linear (ii) ORIGINAL SOURCE:
                (A) ORGANISM: Branhamella catarrhalis
                (B) STRAIN: 25240

(iii) FEATURE:
                (A) LOCATION: CD gene region (complementary strand), 826-842
                (B) IDENTIFICATION METHOD: by experiment
                (C) OTHER INFORMATION: hybridizes to Branhamella catarrhalis gene region (iv) SEQUENCE DESCRIPTION: SEQ ID NO: 8:

GGTTCTGCCA CTGGTGC    17

(2) INFORMATION FOR SEQ ID NO:9:

(i) SEQUENCE CHARACTERISTICS:
                (A) LENGTH: 15 nucleotides
                (B) TYPE: nucleic acid
                (C) STRANDEDNESS: single-stranded
                (D) TOPOLOGY: linear (ii) ORIGINAL SOURCE:
                (A) ORGANISM: Branhamella catarrhalis
                (B) STRAIN: 25240

(iii) FEATURE:
                (A) LOCATION: CD gene region (complementary strand), 1211-1225
                (B) IDENTIFICATION METHOD: by experiment
                (C) OTHER INFORMATION: hybridizes to Branhamella catarrhalis gene region (iv) SEQUENCE DESCRIPTION: SEQ ID NO: 9:

TGTAGCGTGC ACTTG    15

(2) INFORMATION FOR SEQ ID NO:10:

(i) SEQUENCE CHARACTERISTICS:
                (A) LENGTH: 18 nucleotides
                (B) TYPE: nucleic acid
                (C) STRANDEDNESS: single-stranded
                (D) TOPOLOGY: linear (ii) ORIGINAL SOURCE:
                (A) ORGANISM: Branhamella catarrhalis
                (B) STRAIN: 25240

(iii) FEATURE:
                (A) LOCATION: CD gene region, 1387-1404
                (B) IDENTIFICATION METHOD: by experiment (C) OTHER INFORMATION: hybridizes to Branhamella catarrhalis
gene region (iv) SEQUENCE DESCRIPTION: SEQ ID NO: 10:

GCAGTAATCA CTGGTAGC        18

(2) INFORMATION FOR SEQ ID NO:11:

(i) SEQUENCE CHARACTERISTICS:
      (A) LENGTH: 15 nucleotides
      (B) TYPE: nucleic acid
      (C) STRANDEDNESS: single- stranded
      (D) TOPOLOGY: linear (ii) ORIGINAL SOURCE:
      (A) ORGANISM: Branhamella catarrhalis
      (B) STRAIN: 25240

(iii) FEATURE:
      (A) LOCATION: CD gene region (complementary strand), 1483-
      (B) IDENTIFICATION METHOD: by experiment
      (C) OTHER INFORMATION: hybridizes to Branhamella catarrhalis
         gene region (iv) SEQUENCE DESCRIPTION: SEQ ID NO: 11:

TCGATAAGGC TTGAG        15

(2) INFORMATION FOR SEQ ID NO:12:

(i) SEQUENCE CHARACTERISTICS:
      (A) LENGTH: 18 nucleotides
      (B) TYPE: nucleic acid
      (C) STRANDEDNESS: single- stranded
      (D) TOPOLOGY: linear (ii) ORIGINAL SOURCE:
      (A) ORGANISM: Branhamella catarrhalis
      (B) STRAIN: 25240

(iii) FEATURE:
      (A) LOCATION: CD gene region, 1665- 1682
      (B) IDENTIFICATION METHOD: by experiment
      (C) OTHER INFORMATION: hybridizes to Branhamella catarrhalis
         gene region (iv) SEQUENCE DESCRIPTION: SEQ ID NO: 12:

CGGGCATATC GCACGACT        18

(2) INFORMATION FOR SEQ ID NO:13:

(i) SEQUENCE CHARACTERISTICS:
      (A) LENGTH: 20 nucleotides
      (B) TYPE: nucleic acid
      (C) STRANDEDNESS: single- stranded
      (D) TOPOLOGY: linear (ii) ORIGINAL SOURCE:
      (A) ORGANISM: Branhamella catarrhalis
      (B) STRAIN: 25240

(iii) FEATURE:
      (A) LOCATION: CD gene region, 941- 960
      (B) IDENTIFICATION METHOD: by experiment
      (C) OTHER INFORMATION: hybridizes to Branhamella catarrhalis
         gene region (iv) SEQUENCE DESCRIPTION: SEQ ID NO: 13:

TTGTTGATTC AGACGGAGAT        20

(2) INFORMATION FOR SEQ ID NO:14:

(i) SEQUENCE CHARACTERISTICS:

( A ) LENGTH: 1727 nucleotides
( B ) TYPE: nucleic acid
( C ) STRANDEDNESS: single- stranded
( D ) TOPOLOGY: linear ( i i ) MOLECULE TYPE: genomic DNA ( i i i ) HYPOTHETICAL: yes ( i v ) ORIGINAL SOURCE:
    ( A ) ORGANISM: Branhamella catarrhalis
    ( B ) STRAIN: 25240

( v ) IMMEDIATE SOURCE:
    ( A ) LIBRARY: genomic
    ( B ) CLONE: EMBL3 clone 5; SUBCLONE: pCD1

( v i ) FEATURE:
    ( A ) LOCATION: CD gene region
    ( B ) IDENTIFICATION METHOD: by experiment
    ( C ) NAME/KEY: signal sequence of encoded protein
    ( D ) LOCATION: -26 to -1

( v i i ) SEQUENCE DESCRIPTION: SEQ ID NO: 14:

```
GGATCCCGTC GACCTGCAGG TCAACGGATC GCTATGCTAA AATAGGTGCG          50

GTAATCTTGA AAAACCAACC ATTCCTTGGA GGAATTT ATG AAA TTT            96
                                         Met Lys Phe
                                         -26

AAT AAA ATC GCT CTT GCG GTC ATC GCA GCC GTT GCA GCT CCA        138
Asn Lys Ile Ala Leu Ala Val Ile Ala Ala Val Ala Ala Pro
                -15

GTT GCA GCT CCA GTT GCT GCT CAA GCT GGT GTG ACA GTC AGC        180
Val Ala Ala Pro Val Ala Ala Gln Ala Gly Val Thr Val Ser
         -5                  -1   1                   5

CCA CTA CTA CTT GGC TAT CAT TAC ACT GAC GAA GCC CAC AAT        222
Pro Leu Leu Leu Gly Tyr His Tyr Thr Asp Glu Ala His Asn
                 10                  15

GAT CAA CGC AAA ATC TTA CGC ACT GGC AAG AAG CTA GAG CTA        264
Asp Gln Arg Lys Ile Leu Arg Thr Gly Lys Lys Leu Glu Leu
 20              25                  30

GAT GCT ACT AAT GCA CCT GCA CCA GCT AAT GGC GGT GTC GCA        306
Asp Ala Thr Asn Ala Pro Ala Pro Ala Asn Gly Gly Val Ala
         35              40                  45

CTG GAC AGT GAG CTA TGG ACT GGT GCT GCG ATT GGT ATC GAA        348
Leu Asp Ser Glu Leu Trp Thr Gly Ala Ala Ile Gly Ile Glu
             50              55                  60

CTT ACG CCA TCA ACT CAG TTC CAA GTT GAA TAT GGT ATC TCT        390
Leu Thr Pro Ser Thr Gln Phe Gln Val Glu Tyr Gly Ile Ser
                 65                  70                  75

AAC CGT GAT GCA AAA TCT TCA GAC AAA TCT GCA CAT CGC TTT        432
Asn Arg Asp Ala Lys Ser Ser Asp Lys Ser Ala His Arg Phe
                 80                  85

GAT GCT GAG CAA GAA ACC ATC AGC GGT AAC TTT TTG ATT GGT        474
Asp Ala Glu Gln Glu Thr Ile Ser Gly Asn Phe Leu Ile Gly
 90                  95                  100

ACT GAG CAG TTC AGC GGC TAC AAT CCA ACA AAT AAA TTC AAG        516
Thr Glu Gln Phe Ser Gly Tyr Asn Pro Thr Asn Lys Phe Lys
         105                 110                 115

CCC TAT GTC TTG GTT GGT GCA GGT CAA TCT AAA ATT AAA GTA        558
Pro Tyr Val Leu Val Gly Ala Gly Gln Ser Lys Ile Lys Val
             120                 125                 130

AAT GCA ATT GAT GGT TAT ACA GCA GAA GTA GCC AAT GGG CAA        600
Asn Ala Ile Asp Gly Tyr Thr Ala Glu Val Ala Asn Gly Gln
                 135                 140                 145

AAC ATT GCA AAA GAT CAA GCT GTA AAA GCA GGT CAA GAA GTT        642
```

```
              Asn  Ile  Ala  Lys  Asp  Gln  Ala  Val  Lys  Ala  Gly  Gln  Glu  Val
                             150                      155

GCT  GAG  TCT  AAA  GAC  ACC  ATC  GGT  AAC  CTA  GGT  CTT  GGT  GCT       684
Ala  Glu  Ser  Lys  Asp  Thr  Ile  Gly  Asn  Leu  Gly  Leu  Gly  Ala
160                      165                      170

CGC  TAC  TTA  GTC  AAT  GAT  GCC  CTT  GCA  CTT  CGT  GGT  GAA  GCC       726
Arg  Tyr  Leu  Val  Asn  Asp  Ala  Leu  Ala  Leu  Arg  Gly  Glu  Ala
     175                      180                      185

CGT  GCT  ATC  CAT  AAT  TTT  GAT  AAC  AAA  TGG  TGG  GAA  GGC  TTG       768
Arg  Ala  Ile  His  Asn  Phe  Asp  Asn  Lys  Trp  Trp  Glu  Gly  Leu
          190                      195                      200

GCG  TTG  GCT  GGT  TTA  GAG  GTA  ACT  TTG  GGT  GGT  CGT  TTG  GCA       810
Ala  Leu  Ala  Gly  Leu  Glu  Val  Thr  Leu  Gly  Gly  Arg  Leu  Ala
               205                      210                      215

CCT  GCA  GTA  CCA  GTA  GCA  CCA  GTG  GCA  GAA  CCT  GTT  GCT  GAA       852
Pro  Ala  Val  Pro  Val  Ala  Pro  Val  Ala  Glu  Pro  Val  Ala  Glu
                    220                      225

CCA  GTT  GTT  GCT  CCA  GCA  CCT  GTG  ATC  CTT  CCT  AAA  CCA  GAA       894
Pro  Val  Val  Ala  Pro  Ala  Pro  Val  Ile  Leu  Pro  Lys  Pro  Glu
230                      235                      240

CCT  GAG  CCT  GTC  ATT  GAG  GAA  GCA  CCA  GCT  GTA  ATT  GAA  GAT       936
Pro  Glu  Pro  Val  Ile  Glu  Glu  Ala  Pro  Ala  Val  Ile  Glu  Asp
     245                      250                      255

ATT  GTT  GTT  GAT  TCA  GAC  GGA  GAT  GGT  GTG  CCT  GAT  CAT  CTG       978
Ile  Val  Val  Asp  Ser  Asp  Gly  Asp  Gly  Val  Pro  Asp  His  Leu
          260                      265                      270

GAT  GCC  TGC  CCA  GGA  ACT  CCA  GTA  AAC  ACT  GTT  GTT  GAT  CCA      1020
Asp  Ala  Cys  Pro  Glu  Thr  Pro  Val  Asn  Thr  Val  Val  Asp  Pro
               275                      280                      285

CGC  GGT  TGC  CCA  GTA  CAG  GTT  AAT  TTG  GTA  GAA  GAG  CTT  CGC      1062
Arg  Gly  Cys  Pro  Val  Gln  Val  Asn  Leu  Val  Glu  Glu  Leu  Arg
                    290                      295

CAA  GAG  TTG  CGT  GTA  TTC  TTT  GAT  TAT  GAT  AAA  TCA  ATC  ATC      1104
Gln  Glu  Leu  Arg  Val  Phe  Phe  Asp  Tyr  Asp  Lys  Ser  Ile  Ile
300                      305                      310

AAA  CCA  CAA  TAC  CGT  GAA  GAA  GTT  GCT  AAG  GTT  GCT  GCG  CAA      1146
Lys  Pro  Gln  Tyr  Arg  Glu  Glu  Val  Ala  Lys  Val  Ala  Ala  Gln
     315                      320                      325

ATG  CGT  GAA  TTC  CCA  AAT  GCA  ACT  GCA  ACC  ATT  GAA  GGT  CAC      1188
Met  Arg  Glu  Phe  Pro  Asn  Ala  Thr  Ala  Thr  Ile  Glu  Gly  His
          330                      335                      340

GCA  TCA  CGC  GAT  TCA  GCA  CGC  TCA  AGT  GCA  CGC  TAC  AAC  CAG      1230
Ala  Ser  Arg  Asp  Ser  Ala  Arg  Ser  Ser  Ala  Arg  Tyr  Asn  Gln
               345                      350                      355

CGT  CTA  TCT  GAA  GCT  CGT  GCT  AAT  GCT  GTT  AAA  TCA  ATG  CTA      1272
Arg  Leu  Ser  Glu  Ala  Arg  Ala  Asn  Ala  Val  Lys  Ser  Met  Leu
                    360                      365

TCT  AAC  GAA  TTT  GGT  ATC  GCT  CCA  AAC  CGC  CTA  AAT  GCA  GTT      1314
Ser  Asn  Glu  Phe  Gly  Ile  Ala  Pro  Asn  Arg  Leu  Asn  Ala  Val
370                      375                      380

GGT  TAT  GGC  TTT  GAT  CGT  CCT  ATC  GCT  CCA  AAT  ACT  ACT  GCT      1356
Gly  Tyr  Gly  Phe  Asp  Arg  Pro  Ile  Ala  Pro  Asn  Thr  Thr  Ala
     385                      390                      395

GAA  GGT  AAA  GCG  ATG  AAC  CGT  CGT  GTA  GAA  GCA  GTA  ATC  ACT      1398
Glu  Gly  Lys  Ala  Met  Asn  Arg  Arg  Val  Glu  Ala  Val  Ile  Thr
          400                      405                      410

GGT  AGC  AAA  ACA  ACG  ACT  GTT  GAT  CAA  ACC  AAA  GAT  ATG  ATT      1440
Gly  Ser  Lys  Thr  Thr  Thr  Val  Asp  Gln  Thr  Lys  Asp  Met  Ile
               415                      420                      425

GTT  CAA  TAATTGCACA  TGAGTATTTG  GTAATCAGCT  TGAATTCTCA                  1486
Val  Gln
```

```
        Val Gln
            427
```

| | | | | |
|---|---|---|---|---|
| AGCCTTATCG | ATAAAAAGC | CACCTTTTTG | GTGGCTTTTT | TATTTGGTGT | 1536 |
| AAATTTTTGG | TTCAGTTAGA | CTGATTTATG | TTATAATAAG | CGGTTTTCTT | 1586 |
| AGCTTTTGAA | TAAATCAGAT | GAGTTAAGCC | AACTGACTGA | TTTTATCAAT | 1636 |
| TGAGTTATTT | TTAAGCCTTT | TATCAGTTCG | GGCATATCGC | ACGACTATTA | 1686 |
| ATCTTTATAT | GAGTATTTAT | GGCAGACGAC | ATTAAGCATT | T | 1727 |

( 2 ) INFORMATION FOR SEQ ID NO:15:

( i ) SEQUENCE CHARACTERISTICS:
        ( A ) LENGTH: 17 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Branhamella catarrhalis
        ( B ) STRAIN: 25240

( i i i ) FEATURE:
        ( A ) LOCATION: CD gene region (complementary strand), 1430-1446
        ( B ) IDENTIFICATION METHOD: by experiment
        ( C ) OTHER INFORMATION: hybridizes to Branhamella catarrhalis
           gene region ( i v ) SEQUENCE DESCRIPTION: SEQ ID NO: 15:

TTGAACAATC ATATCTT    17

( 2 ) INFORMATION FOR SEQ ID NO:16:

( i ) SEQUENCE CHARACTERISTICS:
        ( A ) LENGTH: 18 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Branhamella catarrhalis
        ( B ) STRAIN: 25240

( i i i ) FEATURE:
        ( A ) LOCATION: CD gene region, 166- 183
        ( B ) IDENTIFICATION METHOD: by experiment
        ( C ) OTHER INFORMATION: hybridizes to Branhamella catarrhalis
           gene region ( i v ) SEQUENCE DESCRIPTION: SEQ ID NO: 16:

GGTGTGACAG TCAGCCCA    18

( 2 ) INFORMATION FOR SEQ ID NO:17:

( i ) SEQUENCE CHARACTERISTICS:
        ( A ) LENGTH: 17 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Branhamella catarrhalis
        ( B ) STRAIN: 25240

( i i i ) FEATURE:
        ( A ) LOCATION: CD gene region (complementary strand), 1081-1097
        ( B ) IDENTIFICATION METHOD: by experiment
        ( C ) OTHER INFORMATION: hybridizes to Branhamella catarrhalis
           gene region ( i v ) SEQUENCE DESCRIPTION: SEQ ID NO: 17:

```
        GATTTATCAT AATCAAA       17
```

( 2 ) INFORMATION FOR SEQ ID NO:18:

( i ) SEQUENCE CHARACTERISTICS:
        ( A ) LENGTH: 17 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Branhamella catarrhalis
        ( B ) STRAIN: 25240

( i i i ) FEATURE:
        ( A ) LOCATION: CD gene region, 1048- 1064
        ( B ) IDENTIFICATION METHOD: by experiment
        ( C ) OTHER INFORMATION: hybridizes to Branhamella catarrhalis
            gene region ( i v ) SEQUENCE DESCRIPTION: SEQ ID NO: 18:

```
        GTAGAAGAGC TTCGCCA       17
```

( 2 ) INFORMATION FOR SEQ ID NO:19:

( i ) SEQUENCE CHARACTERISTICS:
        ( A ) LENGTH: 105 residues
        ( B ) TYPE: amino acid
        ( C ) TOPOLOGY: linear ( i i ) ORIGINAL SOURCE:
        ( A ) ORGANISM: Branhamella catarrhalis
        ( B ) STRAIN: 25240

( i i i ) FEATURE:
        ( A ) LOCATION: CD amino acid positions 1-105

( i v ) SEQUENCE DESCRIPTION: SEQ ID NO: 19:

```
Gly Val Thr Val Ser Pro Leu Leu Leu Gly Tyr His Tyr Thr Asp
 1               5                  10                  15

Glu Ala His Asn Asp Gln Arg Lys Ile Leu Arg Thr Gly Lys Lys
                20                  25                  30

Leu Glu Leu Asp Ala Thr Asn Ala Pro Ala Pro Ala Asn Gly Gly
                35                  40                  45

Val Ala Leu Asp Ser Glu Leu Trp Thr Gly Ala Ala Ile Gly Ile
                50                  55                  60

Glu Leu Thr Pro Ser Thr Gln Phe Gln Val Glu Tyr Gly Ile Ser
                65                  70                  75

Asn Arg Asp Ala Lys Ser Ser Asp Lys Ser Ala His Arg Phe Asp
                80                  85                  90

Ala Glu Gln Glu Thr Ile Ser Gly Asn Phe Leu Ile Gly Thr Glu
                95                  100                 105
```

( 2 ) INFORMATION FOR SEQ ID NO:20:

( i ) SEQUENCE CHARACTERISTICS:
        ( A ) LENGTH: 31 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Branhamella catarrhalis
        ( B ) STRAIN: 25240

( i i i ) SEQUENCE DESCRIPTION: SEQ ID NO: 20:

```
GCGCGCGGAT CCGGTGTGAC AGTCAGCCCA C      31
```

( 2 ) INFORMATION FOR SEQ ID NO:21:

( i ) SEQUENCE CHARACTERISTICS:
        ( A ) LENGTH: 29 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Branhamella catarrhalis
        ( B ) STRAIN: 25240

( i i i ) SEQUENCE DESCRIPTION: SEQ ID NO: 21:

ATATATGAAT TCCTCAGTAC CAATCAAAA     29

( 2 ) INFORMATION FOR SEQ ID NO:22:

( i ) SEQUENCE CHARACTERISTICS:
        ( A ) LENGTH: 97 residues
        ( B ) TYPE: amino acid
        ( C ) TOPOLOGY: linear ( i i ) ORIGINAL SOURCE:
        ( A ) ORGANISM: Branhamella catarrhalis
        ( B ) STRAIN: 25240

( i i i ) FEATURE:
        ( A ) LOCATION: CD amino acid positions 106-202

( i v ) SEQUENCE DESCRIPTION: SEQ ID NO: 22:

```
Gln  Phe  Ser  Gly  Tyr  Asn  Pro  Thr  Asn  Lys  Phe  Lys  Pro  Tyr  Val
 1              5                        10                       15

Leu  Val  Gly  Ala  Gly  Gln  Ser  Lys  Ile  Lys  Val  Asn  Ala  Ile  Asp
              20                        25                       30

Gly  Tyr  Thr  Ala  Glu  Val  Ala  Asn  Gly  Gln  Asn  Ile  Ala  Lys  Asp
              35                        40                       45

Gln  Ala  Val  Lys  Ala  Gly  Gln  Glu  Val  Ala  Glu  Ser  Lys  Asp  Thr
              50                        55                       60

Ile  Gly  Asn  Leu  Gly  Leu  Gly  Ala  Arg  Tyr  Leu  Val  Asn  Asp  Ala
              65                        70                       75

Leu  Ala  Leu  Arg  Gly  Glu  Ala  Arg  Ala  Ile  His  Asn  Phe  Asp  Asn
              80                        85                       90

Lys  Trp  Trp  Glu  Gly  Leu  Ala
              95
```

( 2 ) INFORMATION FOR SEQ ID NO:23:

( i ) SEQUENCE CHARACTERISTICS:
        ( A ) LENGTH: 29 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Branhamella catarrhalis
        ( B ) STRAIN: 25240

( i i i ) SEQUENCE DESCRIPTION: SEQ ID NO: 23:

GCGCGCGGAT CCCAGTTCAG CGGCTACAA     29

( 2 ) INFORMATION FOR SEQ ID NO:24:

( i ) SEQUENCE CHARACTERISTICS:
        ( A ) LENGTH: 30 nucleotides
        ( B ) TYPE: nucleic acid
        ( C ) STRANDEDNESS: single- stranded
        ( D ) TOPOLOGY: linear ( i i ) ORIGINAL SOURCE:
(A) ORGANISM: Branhamella catarrhalis
(B) STRAIN: 25240

( i i i ) SEQUENCE DESCRIPTION: SEQ ID NO: 24:

ATATATGAAT TCCGCCAAGC CTTCCCACCA        30

(2) INFORMATION FOR SEQ ID NO:25:

( i ) SEQUENCE CHARACTERISTICS:
(A) LENGTH: 59 residues
(B) TYPE: amino acid
(C) TOPOLOGY: linear ( i i ) ORIGINAL SOURCE:
(A) ORGANISM: Branhamella catarrhalis
(B) STRAIN: 25240

( i i i ) FEATURE:
(A) LOCATION: CD amino acid positions 203-261

( i v ) SEQUENCE DESCRIPTION: SEQ ID NO: 25:

```
Leu Ala Gly Leu Glu Val Thr Leu Gly Gly Arg Leu Ala Pro Ala
 1               5                  10                  15

Val Pro Val Ala Pro Val Ala Glu Pro Val Ala Glu Pro Val Val
                20                  25                  30

Ala Pro Ala Pro Val Ile Leu Pro Lys Pro Glu Pro Glu Pro Val
                35                  40                  45

Ile Glu Glu Ala Pro Ala Val Ile Glu Asp Ile Val Val Asp
                50                  55              59
```

(2) INFORMATION FOR SEQ ID NO:26:

( i ) SEQUENCE CHARACTERISTICS:
(A) LENGTH: 31 nucleotides
(B) TYPE: nucleic acid
(C) STRANDEDNESS: single-stranded
(D) TOPOLOGY: linear ( i i ) ORIGINAL SOURCE:
(A) ORGANISM: Branhamella catarrhalis
(B) STRAIN: 25240

( i i i ) SEQUENCE DESCRIPTION: SEQ ID NO: 26:

GCGCGCGGAT CCTTGGCTGG TTTAGAGGTA A        31

(2) INFORMATION FOR SEQ ID NO:27:

( i ) SEQUENCE CHARACTERISTICS:
(A) LENGTH: 32 nucleotides
(B) TYPE: nucleic acid
(C) STRANDEDNESS: single-stranded
(D) TOPOLOGY: linear ( i i ) ORIGINAL SOURCE:
(A) ORGANISM: Branhamella catarrhalis
(B) STRAIN: 25240

( i i i ) SEQUENCE DESCRIPTION: SEQ ID NO: 27:

ATATATGAAT TCAACAACAA TATCTTCAAT TA        32

(2) INFORMATION FOR SEQ ID NO:28:

( i ) SEQUENCE CHARACTERISTICS:
(A) LENGTH: 71 residues
(B) TYPE: amino acid
(C) TOPOLOGY: linear ( i i ) ORIGINAL SOURCE:
    ( A ) ORGANISM: Branhamella catarrhalis
    ( B ) STRAIN: 25240

( i i i ) FEATURE:
    ( A ) LOCATION: CD amino acid positions 261-331

( i v ) SEQUENCE DESCRIPTION: SEQ ID NO: 28:

```
Asp Ser Asp Gly Asp Gly Val Pro Asp His Leu Asp Ala Cys Pro
 1           5                   10                      15

Glu Thr Pro Val Asn Thr Val Val Asp Pro Arg Gly Cys Pro Val
            20                  25                      30

Gln Val Asn Leu Val Glu Glu Leu Arg Gln Glu Leu Arg Val Phe
            35                  40                      45

Phe Asp Tyr Asp Lys Ser Ile Ile Lys Pro Gln Tyr Arg Glu Glu
            50                  55                      60

Val Ala Lys Val Ala Ala Gln Met Arg Glu Phe
            65                  70
```

( 2 ) INFORMATION FOR SEQ ID NO:29:

( i ) SEQUENCE CHARACTERISTICS:
        ( A ) LENGTH: 29 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Branhamella catarrhalis
        ( B ) STRAIN: 25240

( i i i ) SEQUENCE DESCRIPTION: SEQ ID NO: 29:

GCGCGCGGAT CCGATTCAGA CGGAGATGG    29

( 2 ) INFORMATION FOR SEQ ID NO:30:

( i ) SEQUENCE CHARACTERISTICS:
        ( A ) LENGTH: 29 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Branhamella catarrhalis
        ( B ) STRAIN: 25240

( i i i ) SEQUENCE DESCRIPTION: SEQ ID NO: 30:

ATATATGAAT TCGAATTCAC GCATTTGCG    29

( 2 ) INFORMATION FOR SEQ ID NO:31:

( i ) SEQUENCE CHARACTERISTICS:
        ( A ) LENGTH: 41 residues
        ( B ) TYPE: amino acid
        ( C ) TOPOLOGY: linear ( i i ) ORIGINAL SOURCE:
        ( A ) ORGANISM: Branhamella catarrhalis
        ( B ) STRAIN: 25240

( i i i ) FEATURE:
        ( A ) LOCATION: CD amino acid positions 261-301

( i v ) SEQUENCE DESCRIPTION: SEQ ID NO: 31:

```
Asp Ser Asp Gly Asp Gly Val Pro Asp His Leu Asp Ala Cys Pro
 1           5                   10                      15

Glu Thr Pro Val Asn Thr Val Val Asp Pro Arg Gly Cys Pro Val
            20                  25                      30
```

```
Gln Val Asn Leu Val Glu Glu Leu Arg Gln Glu
             35                  40
```

( 2 ) INFORMATION FOR SEQ ID NO:32:

( i ) SEQUENCE CHARACTERISTICS:
        ( A ) LENGTH: 29 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Branhamella catarrhalis
        ( B ) STRAIN: 25240

( i i i ) SEQUENCE DESCRIPTION: SEQ ID NO: 32:

```
ATATATGAAT TCATCCAGAT GATCAGGCA     29
```

( 2 ) INFORMATION FOR SEQ ID NO:33:

( i ) SEQUENCE CHARACTERISTICS:
        ( A ) LENGTH: 26 residues
        ( B ) TYPE: amino acid
        ( C ) TOPOLOGY: linear ( i i ) ORIGINAL SOURCE:
        ( A ) ORGANISM: Branhamella catarrhalis
        ( B ) STRAIN: 25240

( i i i ) FEATURE:
        ( A ) LOCATION: CD amino acid positions 286-311

( i v ) SEQUENCE DESCRIPTION: SEQ ID NO: 33:

```
Arg Gly Cys Pro Val Gln Val Asn Leu Val Glu Glu Leu Arg Gln
 1               5                   10                  15

Glu Leu Arg Val Phe Phe Asp Tyr Asp Lys Ser
             20                  25
```

( 2 ) INFORMATION FOR SEQ ID NO:34:

( i ) SEQUENCE CHARACTERISTICS:
        ( A ) LENGTH: 29 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Branhamella catarrhalis
        ( B ) STRAIN: 25240

( i i i ) SEQUENCE DESCRIPTION: SEQ ID NO: 34:

```
GCGCGCGGAT CCCGCGGTTG CCCAGTACA     29
```

( 2 ) INFORMATION FOR SEQ ID NO:35:

( i ) SEQUENCE CHARACTERISTICS:
        ( A ) LENGTH: 29 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Branhamella catarrhalis
        ( B ) STRAIN: 25240

( i i i ) SEQUENCE DESCRIPTION: SEQ ID NO: 35:

```
ATATATGAAT TCGATTTATC ATAATCAAA     29
```

( 2 ) INFORMATION FOR SEQ ID NO:36:

( i ) SEQUENCE CHARACTERISTICS:
  ( A ) LENGTH: 16 residues
  ( B ) TYPE: amino acid
  ( C ) TOPOLOGY: linear ( i i ) ORIGINAL SOURCE:
  ( A ) ORGANISM: Branhamella catarrhalis
  ( B ) STRAIN: 25240

( i i i ) FEATURE:
  ( A ) LOCATION: CD amino acid positions 286-301

( i v ) SEQUENCE DESCRIPTION: SEQ ID NO: 36:

```
Arg Gly Cys Pro Val Gln Val Asn Leu Val Glu Glu Leu Arg Gln
 1               5                   10                  15
Glu
```

( 2 ) INFORMATION FOR SEQ ID NO:37:

( i ) SEQUENCE CHARACTERISTICS:
  ( A ) LENGTH: 30 nucleotides
  ( B ) TYPE: nucleic acid
  ( C ) STRANDEDNESS: single-stranded
  ( D ) TOPOLOGY: linear ( i i ) ORIGINAL SOURCE:
  ( A ) ORGANISM: Branhamella catarrhalis
  ( B ) STRAIN: 25240

( i i i ) SEQUENCE DESCRIPTION: SEQ ID NO: 37:

ATATATGAAT TCCTCTTGGC GAAGCTCTTC     30

( 2 ) INFORMATION FOR SEQ ID NO:38:

( i ) SEQUENCE CHARACTERISTICS:
  ( A ) LENGTH: 11 residues
  ( B ) TYPE: amino acid
  ( C ) TOPOLOGY: linear ( i i ) ORIGINAL SOURCE:
  ( A ) ORGANISM: Branhamella catarrhalis
  ( B ) STRAIN: 25240

( i i i ) FEATURE:
  ( A ) LOCATION: CD amino acid positions 293-303

( i v ) SEQUENCE DESCRIPTION: SEQ ID NO: 38:

```
Asn Leu Val Glu Glu Leu Arg Gln Glu Leu Arg
 1               5                   10
```

( 2 ) INFORMATION FOR SEQ ID NO:39:

( i ) SEQUENCE CHARACTERISTICS:
  ( A ) LENGTH: 29 nucleotides
  ( B ) TYPE: nucleic acid
  ( C ) STRANDEDNESS: single-stranded
  ( D ) TOPOLOGY: linear ( i i ) ORIGINAL SOURCE:
  ( A ) ORGANISM: Branhamella catarrhalis
  ( B ) STRAIN: 25240

( i i i ) SEQUENCE DESCRIPTION: SEQ ID NO: 39:

GCGCGCGGAT CCAATTTGGT AGAAGAGCT     29

( 2 ) INFORMATION FOR SEQ ID NO:40:

( i ) SEQUENCE CHARACTERISTICS:
  ( A ) LENGTH: 29 nucleotides
  ( B ) TYPE: nucleic acid ( C ) STRANDEDNESS: single-stranded
( D ) TOPOLOGY: linear ( i i ) ORIGINAL SOURCE:
( A ) ORGANISM: Branhamella catarrhalis
( B ) STRAIN: 25240

( i i i ) SEQUENCE DESCRIPTION: SEQ ID NO: 40:

ATATATGAAT TCACGCAACT CTTGGCGAA          29

( 2 ) INFORMATION FOR SEQ ID NO:41:

( i ) SEQUENCE CHARACTERISTICS:
( A ) LENGTH: 17 residues
( B ) TYPE: amino acid
( C ) TOPOLOGY: linear ( i i ) ORIGINAL SOURCE:
( A ) ORGANISM: Branhamella catarrhalis
( B ) STRAIN: 25240

( i i i ) FEATURE:
( A ) LOCATION: CD amino acid positions 295-311

( i v ) SEQUENCE DESCRIPTION: SEQ ID NO: 41:

Val Glu Glu Leu Arg Gln Glu Leu Arg Val Phe Phe Asp Tyr Asp
 1               5                   10                  15

Lys Ser
   17

( 2 ) INFORMATION FOR SEQ ID NO:42:

( i ) SEQUENCE CHARACTERISTICS:
( A ) LENGTH: 29 nucleotides
( B ) TYPE: nucleic acid
( C ) STRANDEDNESS: single-stranded
( D ) TOPOLOGY: linear ( i i ) ORIGINAL SOURCE:
( A ) ORGANISM: Branhamella catarrhalis
( B ) STRAIN: 25240

( i i i ) SEQUENCE DESCRIPTION: SEQ ID NO: 42:

GCGCGCGGAT CCGTAGAAGA GCTTCGCCA          29

( 2 ) INFORMATION FOR SEQ ID NO:43:

( i ) SEQUENCE CHARACTERISTICS:
( A ) LENGTH: 29 nucleotides
( B ) TYPE: nucleic acid
( C ) STRANDEDNESS: single-stranded
( D ) TOPOLOGY: linear ( i i ) ORIGINAL SOURCE:
( A ) ORGANISM: Branhamella catarrhalis
( B ) STRAIN: 25240

( i i i ) SEQUENCE DESCRIPTION: SEQ ID NO: 43:

ATATATGAAT TCGATTTATC ATAATCAAA          29

( 2 ) INFORMATION FOR SEQ ID NO:44:

( i ) SEQUENCE CHARACTERISTICS:
( A ) LENGTH: 21 residues
( B ) TYPE: amino acid
( C ) TOPOLOGY: linear ( i i ) ORIGINAL SOURCE:
( A ) ORGANISM: Branhamella catarrhalis
( B ) STRAIN: 25240

( i i i ) FEATURE:
    ( A ) LOCATION: CD amino acid positions 311-331

( i v ) SEQUENCE DESCRIPTION: SEQ ID NO: 44:

Ser Ile Ile Lys Pro Gln Tyr Arg Glu Glu Val Ala Lys Val Ala
 1            5                    10                   15

Ala Gln Met Arg Glu Phe
             20

( 2 ) INFORMATION FOR SEQ ID NO:45:

( i ) SEQUENCE CHARACTERISTICS:
        ( A ) LENGTH: 29 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Branhamella catarrhalis
        ( B ) STRAIN: 25240

( i i i ) SEQUENCE DESCRIPTION: SEQ ID NO: 45:

GCGCGCGGAT CCTCAATCAT CAAACCCCA          29

( 2 ) INFORMATION FOR SEQ ID NO:46:

( i ) SEQUENCE CHARACTERISTICS:
        ( A ) LENGTH: 29 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Branhamella catarrhalis
        ( B ) STRAIN: 25240

( i i i ) SEQUENCE DESCRIPTION: SEQ ID NO: 46:

ATATATGAAT TCGAATTCAC GCATTTGCG          29

( 2 ) INFORMATION FOR SEQ ID NO:47:

( i ) SEQUENCE CHARACTERISTICS:
        ( A ) LENGTH: 59 residues
        ( B ) TYPE: amino acid
        ( C ) TOPOLOGY: linear ( i i ) ORIGINAL SOURCE:
        ( A ) ORGANISM: Branhamella catarrhalis
        ( B ) STRAIN: 25240

( i i i ) FEATURE:
        ( A ) LOCATION: CD amino acid positions 332-390

( i v ) SEQUENCE DESCRIPTION: SEQ ID NO: 47:

Pro Asn Ala Thr Ala Thr Ile Glu Gly His Ala Ser Arg Asp Ser
 1            5                    10                   15

Ala Arg Ser Ser Ala Arg Tyr Asn Gln Arg Leu Ser Glu Ala Arg
             20                  25                   30

Ala Asn Ala Val Lys Ser Met Leu Ser Asn Glu Phe Gly Ile Ala
             35                  40                   45

Pro Asn Arg Leu Asn Ala Val Gly Tyr Gly Phe Asp Arg Pro
             50                  55                   59

( 2 ) INFORMATION FOR SEQ ID NO:48:

( i ) SEQUENCE CHARACTERISTICS:
        ( A ) LENGTH: 29 nucleotides
        ( B ) TYPE: nucleic acid ( C ) STRANDEDNESS: single-stranded
( D ) TOPOLOGY: linear ( i i ) ORIGINAL SOURCE:
( A ) ORGANISM: Branhamella catarrhalis
( B ) STRAIN: 25240

( i i i ) SEQUENCE DESCRIPTION: SEQ ID NO: 48:

GCGCGCGGAT CCCCAAATGC AACTGCAAC    29

( 2 ) INFORMATION FOR SEQ ID NO:49:

( i ) SEQUENCE CHARACTERISTICS:
( A ) LENGTH: 29 nucleotides
( B ) TYPE: nucleic acid
( C ) STRANDEDNESS: single-stranded
( D ) TOPOLOGY: linear ( i i ) ORIGINAL SOURCE:
( A ) ORGANISM: Branhamella catarrhalis
( B ) STRAIN: 25240

( i i i ) SEQUENCE DESCRIPTION: SEQ ID NO: 49:

ATATATGAAT CCAGGACGAT CAAAGCCAT    29

( 2 ) INFORMATION FOR SEQ ID NO:50:

( i ) SEQUENCE CHARACTERISTICS:
( A ) LENGTH: 37 residues
( B ) TYPE: amino acid
( C ) TOPOLOGY: linear ( i i ) ORIGINAL SOURCE:
( A ) ORGANISM: Branhamella catarrhalis
( B ) STRAIN: 25240

( i i i ) FEATURE:
( A ) LOCATION: CD amino acid positions 391-427

( i v ) SEQUENCE DESCRIPTION: SEQ ID NO: 50:

```
Ile Ala Pro Asn Thr Thr Ala Glu Gly Lys Ala Met Asn Arg Arg
 1               5                  10                  15

Val Glu Ala Val Ile Thr Gly Ser Lys Thr Thr Val Asp Gln
                20                  25                  30

Thr Lys Asp Met Ile Val Gln
                35       37
```

( 2 ) INFORMATION FOR SEQ ID NO:51:

( i ) SEQUENCE CHARACTERISTICS:
( A ) LENGTH: 29 nucleotides
( B ) TYPE: nucleic acid
( C ) STRANDEDNESS: single-stranded
( D ) TOPOLOGY: linear ( i i ) ORIGINAL SOURCE:
( A ) ORGANISM: Branhamella catarrhalis
( B ) STRAIN: 25240

( i i i ) SEQUENCE DESCRIPTION: SEQ ID NO: 51:

GCGCGCGGAT CCATCGCTCC AAATACTAC    29

( 2 ) INFORMATION FOR SEQ ID NO:52:

( i ) SEQUENCE CHARACTERISTICS:
( A ) LENGTH: 33 nucleotides
( B ) TYPE: nucleic acid
( C ) STRANDEDNESS: single-stranded
( D ) TOPOLOGY: linear (ii) ORIGINAL SOURCE:
  (A) ORGANISM: Branhamella catarrhalis
  (B) STRAIN: 25240

(iii) SEQUENCE DESCRIPTION: SEQ ID NO: 52:

ATATATGAAT TCTTGAACAA TCATATCTTT GGT        33

VACCINE FOR BRANHAMELLA CATARRHALIS

This application is a continuation-in-part of my earlier application U.S. Ser. No. 08/129,719, filed Sep. 29, 1993, now U.S. Pat. No. 5,556,755, issued Sep. 17, 1996, which is incorporated herein by reference.

This invention was made with government support under grant A128304 awarded by the National Institutes of Health. The government has certain rights in the invention.

FIELD OF INVENTION

The present invention relates to compositions comprising a protein, and peptides and oligopeptides thereof, associated with the outer membrane of *Branhamella catarrhalis*. More particularly, the invention is directed to compositions of a protein, and peptides and oligopeptides thereof, related to an outer membrane protein,"CD", of apparent molecular mass of about 55,000 to 60,000 daltons found in *B. catarrhalis*. Also disclosed is methods for preparing CD and CD peptides using recombinant DNA and/or biochemical techniques. Related thereto, disclosed is the DNA sequence encoding CD, and recombinant vectors useful in directing the expression of CD and CD peptides and oligopeptides, and host cells transformed with such recombinant vectors.

The proteins, peptides, and oligopeptides are used as immunogens in vaccine formulations for active immunization; and can be used to generate protein-specific and peptide-specific antisera useful for passive immunization, and as reagents for diagnostic assays. The nucleotide sequences disclosed provide for the synthesis of corresponding oligonucleotides which can be used as reagents in diagnostic assays directed to the detection of *B. catarrhalis* genetic material, and incorporated into expression vectors for use as genetic vaccine formulations.

BACKGROUND OF THE INVENTION

*Branhamella catarrhalis* (also known as *Moraxella catarrhalis*) is an important human respiratory tract pathogen. *B. catarrhalis* is the third most common cause of otitis media in infants and children, after *Streptococcus pneumoniae* and nontypeable *Haemophilus influenzae*, as documented in studies in which tympanocentesis has been used to establish the etiologic agent (Murphy, 1989, *Pediatr. Infect. Dis. J.* 8:S75-S77). *B. catarrhalis* is a common cause of sinusitis and conjunctivitis in both children and adults (See for example, Bluestone, 1986, *Drugs* 31:S132-S141; Brorson et al., 1976, *Scand. J. Infect. Dis.* 8:151-155; and Romberger et al., 1987, *South. Med. J.* 80:926-928); and is an important cause of lower respiratory tract infections in adults with chronic bronchitis and chronic obstructive pulmonary disease (Murphy et al., 1992, *Am. Rev. Respir. Dis.* 146:1067-1083; Carlin, 1990, *Clin. Microbiol. Rev.* 3:293-320). Additionally, *B. catarrhalis* can cause pneumonia, endocarditis, septicemia, and meningitis in immunocompromised hosts (Cocchi et al., 1968, *Acta Paediatr. Scand.* 57:451-3; Douer et al., 1977, *Ann. Intern. Med.* 86:116-119; McNeely et al., 1976, *Am. Rev. Respir. Dis.* 114:399-402).

Since recurrent otitis media is associated with substantial morbidity, there is interest in identifying strategies for preventing these infections. One such approach is the development of vaccines. An effective vaccine for preventing bacterial otitis media would need to include antigens which would generate protection against infection by *S. pneumoniae*, nontypeable *H. influenzae* and *B. catarrhalis*. Indeed, vaccine development for the pneumococcus and nontypeable *H. influenzae* are progressing such that potentially protective antigens have been identified and are currently undergoing testing (See for example, Murphy et al., U.S. Pat. No. 5,173,294; and Vella et al., 1992, *Infect. Immun.* 60:4977-4983). As these vaccines are developed and used more widely, the relative importance of *B. catarrhalis* as a cause of otitis media will increase in the next decade. Besides infants and children benefitting from a vaccine to prevent otitis media caused by *B. catarrhalis*, adults with chronic obstructive pulmonary disease, and immunocompromised children and adults would benefit from a vaccine to prevent infections caused by *B. catarrhalis*.

Bacterial components which have been investigated as potential vaccine antigens include polysaccharides, lipopolysaccharides or modifications thereof, and outer membrane proteins. In general, as exemplified by the type b capsular polysaccharide of *H. influenzae*, polysaccharide antigens have been shown to be a poor immunogen in children under the age of 18 months. Active immunization with lipopolysaccharide (LPS) is unacceptable due to its inherent toxicity. The pathophysiologic effects of LPS may include fever, leucopenia, leucocytosis, the Schwartzman reaction, disseminated intravascular coagulation, and in large doses, shock and death. In general, proteins are immunogenic in infants around three months of age. Thus, outer membrane proteins are being investigated as possible vaccine antigens.

While recent studies have begun to focus on outer membrane proteins of *B. catarrhalis*, little is known about the antigenic and molecular structure of these proteins. Studies of purified outer membranes by SDS-PAGE have revealed a rather homogeneous pattern among strains of the bacterium (Bartos and Murphy, 1988, *J. Infect. Dis.* 158:761-765). Eight major outer membrane proteins, designated by the letters A-H, have been identified (Murphy et al., 1989, *Microbial Pathogen.* 6:159-174; Bartos et al., 1988, *J. Infect. Dis.* 158: 761-765). Outer membrane proteins C and D differ slightly in apparent molecular mass, and thus appear as a doublet on SDS-PAGE electrophoresis. Monoclonal antibodies have been developed to *B. catarrhalis* resulting in two monoclonal antibodies, 7D6 and 5E8, which recognized both proteins C and D (Sarwar et al., 1992, *Infect. Immun.* 60:804-809). Prior to the development of the present invention, it was unknown whether this doublet represented a single protein (CD) with two stable conformations, or whether C and D are two closely related proteins encoded by different genes (Sarwar et al., supra). Proteins C and D are of interest, particularly for vaccine development, because these proteins express at least one conserved epitope on the surface of intact *B. catarrhalis* (Sarwar et al., 1992, supra).

Hence, with the increasing recognition of *B. catarrhalis* as an important bacterial pathogen, there is a need for a vaccine that is immunogenic in children and adults. Such a vaccine would have to be directed to a bacterial component which has a surface-exposed epitope on intact bacteria, wherein the epitope is conserved amongst strains of *B. catarrhalis*.

SUMMARY OF THE INVENTION

The present invention is directed to a protein and peptides related to an outer membrane protein having an apparent molecular mass of about 55,000 to 60,000 daltons of *B. catarrhalis*, wherein the protein was formerly thought to be two related proteins, C and D, but which through recombinant DNA techniques disclosed herein, is now known to be one protein, CD, which is heat modifiable resulting in the appearance of two proteins differing by migration in SDS gels. The CD protein, and peptides (herein termed "CD peptides") and oligopeptides (herein termed "CD oligopeptides") thereof, of the present invention may be used as immunogens in prophylactic and/or therapeutic vaccine formulations; or as an antigen in diagnostic immunoassays directed to detection of B. catarrhalis infection by measuring an increase in serum titer of B. catarrhalis-specific antibody. Also, CD protein, CD peptides, and CD oligopeptides of the present invention may be used to generate CD-specific antibody which may be useful for passive immunization and as reagents for diagnostic assays directed to detecting the presence of B. catarrhalis in clinical specimens. CD peptides or CD oligopeptides can be obtained by chemical synthesis, purification from B. catarrhalis, or produced from recombinant vector expression systems using the nucleic acid sequences disclosed herein.

One embodiment of the present invention is directed to the construction of novel DNA sequences and vectors including plasmid DNA, and viral DNA such as human viruses, animal viruses, insect viruses, or bacteriophages which can be used to direct the expression of CD protein, CD peptides, or CD oligopeptides in appropriate host cells from which the expressed protein or peptides may be purified.

Another embodiment of the present invention also provides methods for molecular cloning of the gene encoding CD, and gene fragments encoding CD peptides or CD oligopeptides. The nucleic acid sequences of the present invention can be used in molecular diagnostic assays for B. catarrhalis genetic material through nucleic acid hybridization, and including the synthesis of CD sequence-specific oligonucleotides for use as primers and/or probes in amplifying, and detecting amplified, nucleic acids.

Additionally, CD protein, CD peptides, and CD oligopeptides can be used as immunogens in prophylactic and/or therapeutic vaccine formulations against pathogenic strains of B. catarrhalis, whether the immunogen is chemically synthesized, purified from B. catarrhalis, or purified from a recombinant expression vector system. Alternatively, the gene encoding CD, or one or more gene fragments encoding CD peptides or CD oligopeptides, may be incorporated into a bacterial or viral vaccine comprising recombinant bacteria or virus which is engineered to produce one or more immunogenic epitopes of CD by itself, or in combination with immunogenic epitopes of other pathogenic microorganisms. In addition, the gene encoding CD or one or more gene fragments encoding CD peptides or CD oligopeptides, operatively linked to one or more regulatory elements, can be introduced directly into humans to express protein CD, CD peptide, or CD oligopeptides to elicit a protective immune response.

DETAILED DESCRIPTION OF THE INVENTION

Figure 1:
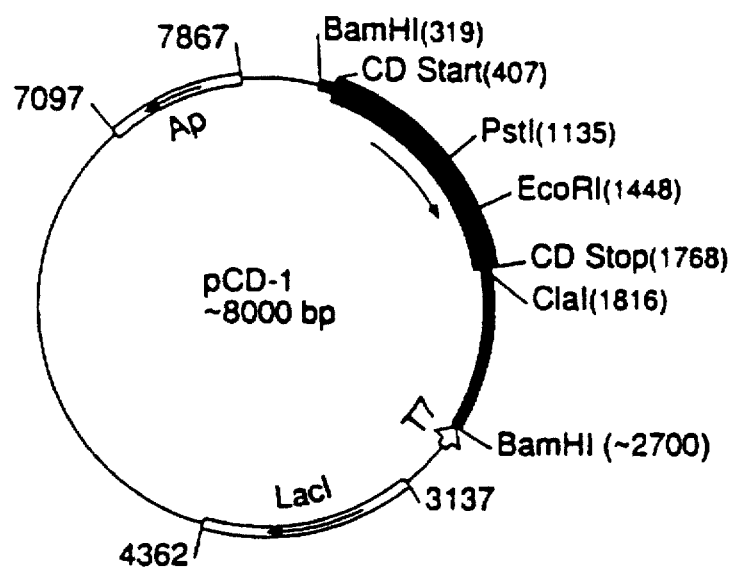
FIG. 1 represents a map of plasmid pCD-1, constructed from pET11b and a 2.4 kb fragment containing the gene which encodes CD. The shaded region represents the DNA insert and the thicker shaded region represents the CD gene. Abbreviations used are as follows: Ap: ampicillin resistance coding region; Lac: lac operon; bp: base pairs.

The present invention is directed to compositions of a bacterial outer membrane protein, and peptides thereof, of B. catarrhalis wherein the protein has been designated "CD". Using SDS-PAGE, the CD protein migrates as a doublet of two bands, characteristic of a heat-modifiable protein, with an apparent molecular mass of about 55,000 to 60,000 daltons. As indicated by one nucleotide sequence of the present invention (SEQ ID NO.14), the gene encoding CD reveals that the predicted amino acid sequence of the mature CD protein has a calculated molecular mass of about 45,788 daltons. The CD protein, CD peptides, and CD oligopeptides of the present invention can be produced using recombinant DNA methods as illustrated herein, or can be synthesized chemically from the amino acid sequence disclosed in the present invention. Additionally, peptides can be produced from enzymatic or chemical cleavage of the mature protein. CD protein, CD peptides, and CD oligopeptides with an immunogenic epitope(s), can be used as immunogens in various vaccine formulations in the prevention of otitis media, sinusitis, conjunctivitis, and lower respiratory tract infections caused by *B. catarrhalis*. Additionally, according to the present invention, the CD protein and CD peptides produced may be used to generate *B. catarrhalis*-specific antisera useful for passive immunization against infections caused by *B. catarrhalis*.

The present invention further provides the nucleotide sequence of the gene encoding CD, as well as the amino acid sequence deduced from the isolated gene. According to one embodiment of the present invention, using recombinant DNA techniques the gene encoding CD, or gene fragments encoding one or more CD peptides having an immunogenic epitope(s), is incorporated into an expression vector, and the recombinant vector is introduced into an appropriate host cell thereby directing the expression of these sequences in that particular host cell. The expression system, comprising the recombinant vector introduced into the host cell, can be used (a) to produce CD protein, CD peptides and CD oligopeptides which can be purified for use as an immunogen in vaccine formulations; (b) to produce CD protein, CD peptides, and CD oligopeptides to be used as an antigen for diagnostic immunoassays or for generating *B. catarrhalis*-specific antisera of therapeutic and/or diagnostic value; c) or if the recombinant expression vector is a live virus such as vaccinia virus, the vector itself may be used as a live or inactivated vaccine preparation to be introduced into the host's cells for expression of CD or immunogenic CD peptides or CD oligopeptides; d) for introduction into live attenuated bacterial cells which are used to express CD protein, CD peptides or CD oligopeptides to vaccinate individuals; e) or for introduction directly into an individual to immunize against the encoded and expressed CD protein, CD peptide, or CD oligopeptide.

For purposes of the description, the methods and compounds of the present invention will be illustrated in the following embodiments:

Embodiment A—Molecular cloning and sequencing of the gene encoding CD, and vectors expressing CD epitopes;

Embodiment B—Conservation of the gene encoding CD amongst *B. catarrhalis* strains;

Embodiment C—Methods for using CD-specific nucleotide sequences in molecular diagnostic assays for the detection of *B. catarrhalis*;

Embodiment D—Characterization of CD including generation of CD peptides;

Embodiment E—Methods for using CD, or CD peptides, in diagnostic immunoassays;

Embodiment F—Methods and compounds for vaccine formulations related to CD and CD peptides.

EMBODIMENT A

Molecular cloning and sequencing of the gene encoding CD, and vectors expressing CD epitopes.

The strategy used was to isolate genomic DNA from *B. catarrhalis*, cleave the isolated DNA into fragments, construct a genomic library comprising insertion of the fragments into an expression vector, introduce the recombinant vectors into the appropriate host cell, and immunoscreen for host cell clones expressing CD-specific epitopes by using CD-specific antisera. *Branhamella catarrhalis* strain 25240, obtained from the American Type Culture Collection (ATCC) was used as the source of bacterial genomic DNA. *B. catarrhalis* was grown on chocolate agar plates at 37° C. in 5% $CO_2$ or in brain heart infusion broth. *Escherichia coli* (*E. coli*) Y1090 was used as the host strain for the bacteriophage lambda gt11 genomic library. Depending on the circumstances, *E. coli* was grown in LB broth, or on LB agar containing 50 µg/ml of ampicillin. Monoclonal antibodies used for immunoscreening clones included 5E8 and 7D6 which recognize different epitopes on the CD outer membrane protein of *B. catarrhalis* (Sarwar et al., supra). Antibody 5E8 is an IgM and recognizes an epitope which is exposed on the surface of the intact bacterium. Antibody 7D6 is an IgG2a and binds an epitope which is not accessible on the bacterial surface.

A lambda gt11 library was constructed with genomic DNA of *B. catarrhalis* 25240 using previously described methods (Nelson et al., 1988, *Infect. Immun.* 56:128–134). Genomic DNA fragments of 2 to 8 kilobases (kb) in size were eluted from an agarose gel and ligated to phage arms. A portion of the library was introduced into *E. coli* Y1090 and the resultant plaques were transferred onto nitrocellulose discs and immunoscreened with monoclonal antibodies 5E8 and 7D6. After incubation with the monoclonal antibodies overnight, the discs were incubated with protein A peroxidase and anti-mouse IgM peroxidase conjugate, with subsequent substrate development, to identify immunoreactive plaques. Screening of a total of approximately 554,000 plaques yielded a clone which contained a 387 base pair insert expressing the epitopes recognized by antibodies 7D6 and 5E8. Nucleotide sequence analysis of the insert contained within this clone showed an open reading frame with no start or stop codons (SEQ ID No. 1). The nucleotide sequence of this clone corresponds to nucleotides 775–1160 of SEQ ID NO. 14 that contains the whole gene sequence encoding CD. The peptide produced by this clone, as shown in SEQ ID NO. 1, corresponds to amino acids 203–331 in the mature protein depicted in SEQ ID NO. 14.

Since several rounds of screening of the lambda gt11 genomic library yielded a small fragment of the CD gene, an EMBL3 library was constructed with genomic DNA of *B. catarrhalis* 25240 with insert sizes of approximately 9 to 23 kb. This library was immunoscreened with monoclonal antibodies 5E8 and 7D6. The EMBL3 genomic library was constructed with methods known in the art (Ausubel et al., 1989, Current Protocols in Molecular Biology, published by John Wiley and Sons) and according to the recommendations of the manufacturer (Stratagene, LaJolla, Calif.). Briefly, genomic DNA of *B. catarrhalis* 25240 was purified using SDS, proteinase K and CTAB. The purified genomic DNA was partially digested with Sau3A to generate varying-size fragments. The DNA fragments were separated by sucrose gradient centrifugation on a 10 to 40% sucrose gradient. The fractions containing fragments of approximately 9 to 23 kilobases in size were dephosphorylated using calf alkaline phosphatase, and precipitated with ethanol to prepare for ligation to EMBL3 arms. Approximately 0.7 µg of these genomic DNA fragments were ligated to 1 µg of EMBL3 arms by using T4 DNA ligase. The ligated phage arms and inserts were packaged into phage and the titer of the library was determined by plating on *E. coli* P2 392, the host strain for the lambda EMBL3 genomic library. The EMBL3 genomic library was immunoscreened with monoclonal antibodies 5E8 and 7D6 as described above.

Immunoscreening of approximately 3500 plaques from the EMBL library yielded a single reactive plaque, designated clone 5. The purified clone was assayed with antibodies 5E8 and 7D6 individually and was reactive with both antibodies. Control experiments showed that the protein A and anti-mouse IgM peroxidase conjugates did not bind to plaques of clone 5.

Phage DNA from clone 5 was purified and digested with SalI to excise the insert. Agarose gel electrophoresis revealed that clone 5 had an insert of 13 kb. The insert was digested with several restriction enzymes and a Southern blot assay was performed. The blot was probed with an oligonucleotide corresponding to DNA sequence from the 387 bp fragment of the CD gene recovered from the lambda gt11 library. The gene encoding CD was determined to be localized to a 2.4 kb NcoI-SalI fragment. The 2.4 kb fragment was subcloned into the BamHI site of pET11b (Novagen, Madison, Wis.) by ligating BamHI linkers onto the insert after its ends were made blunt with Klenow DNA polymerase. The resulting plasmid, which contained a 2.4 kb insert, was called pCD1 (FIG. 1). Plasmid pET11b, and recombinant pCD1 were propagated in E. coli HB101 on LB agar containing 50 µg/ml of ampicillin. A whole cell lysate of transformants containing pCD1 was subjected to SDS-PAGE and immunoblot assay with antibodies 7D6 and 5E8. The results indicate that pCD1 encodes a full length CD protein which is reactive with both antibodies.

Dideoxy sequencing of both strands of 1727 bp of the 2.4 kb insert of pCD1 was performed with the aid of additional oligonucleotides synthesized to correspond to sequence at appropriate intervals within the insert such as represented by SEQ ID NOs. 2-13. An open reading frame of 453 amino acids, which represents a protein of 48,277 daltons, was identified (SEQ ID NO. 14). A strong transcriptional terminator was present beginning 54 bp downstream of the stop codon.

Figure 2:
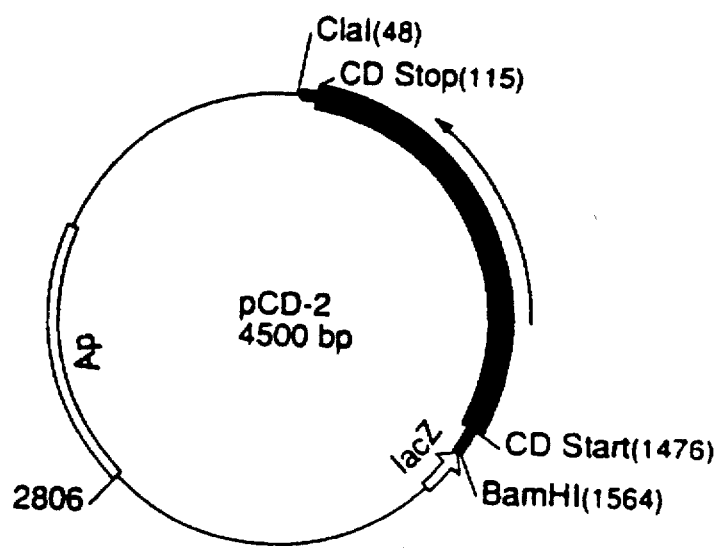
FIG. 2 represents a map of plasmid pCD-2, constructed from pGEM7zf- and a 1.5 kb fragment containing the gene which encodes CD. The shaded region represents the DNA insert and the thicker shaded region represents the gene encoding CD. Abbreviations used are as follows: Ap: ampicillin resistance coding region; Lac: lac operon; bp: base pairs.
Figure 3:
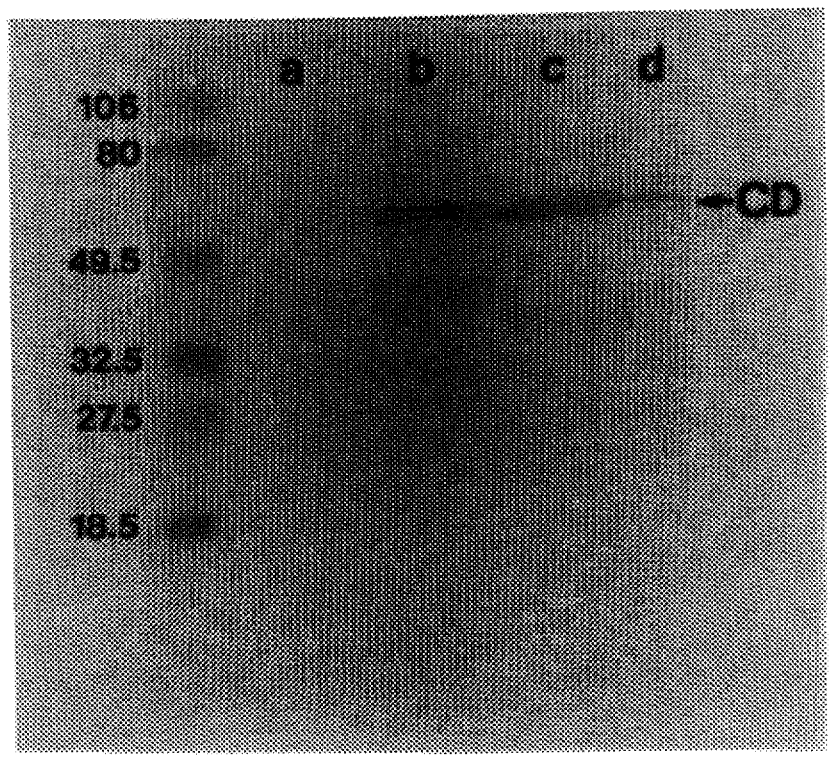
FIG. 3 represents an immunoblot assay with whole cell lysates of: lane a: E. coli HB101 transformed with pGEM7zf-; lane b: E. coli HB101 transformed with pCD-2 which contains the gene encoding CD; and lanes c and d: B. catarrhalis strain 25240. Lanes b and c contain similar amounts of protein (~20 µg) while, lane d contains less protein to show the characteristic doublet of CD. Samples were incubated at 100° C. for 10 minutes in sample buffer containing 0.06M Tris, 1.2% sodium dodecyl sulfate (SDS), 12% glycerol, and 5.8% β-mercaptoethanol. The immunoblot was developed with antibody 5E8 which recognizes an epitope on the CD protein. Molecular mass markers are noted on the left in thousands of daltons.

The calculated molecular mass of the mature protein (45,788 daltons) differed significantly from the apparent molecular mass of OMP CD observed in SDS-PAGE (60,000 or 55,000, daltons in reduced or nonreduced form, respectively). Therefore, a plasmid containing the open reading frame without downstream sequence was constructed to determine whether expression of the reading frame would yield a full size CD protein. A ClaI site is located 48 bp downstream of the open reading frame. A BamHI-ClaI DNA fragment of 1558 bp containing the putative CD gene was subcloned into pGEM7zf- (Promega Corp., Madison, Wis.) in constructing new plasmid pCD2 (FIG. 2). By immunoblot assay, shown in FIG. 3 (lane b), E. coli transformants containing pCD2 express a full-size CD protein. In addition, the immunoblot assay shows that the CD gene product migrates as a doublet (lane b), indicating that both bands represent products of a single gene rather than representing two related proteins produced by their respective genes.

Thus, this embodiment illustrates that nucleotide sequences encoding CD or portions thereof, can be inserted into, and expressed by various vectors including phage vectors and plasmids. Successful expression of the protein and peptides requires that either the insert comprising the gene or gene fragment, or the vector itself, contain the necessary elements for transcription and translation which is compatible with, and recognized by the particular host system used for expression. DNA encoding CD protein, CD peptides, or CD oligopeptides can be synthesized or isolated and sequenced using the methods and primer sequences as illustrated according to Embodiments A, B, and D herein. A variety of host systems may be utilized to express CD protein, CD peptides or CD oligopeptides, which include, but are not limited to bacteria transformed with a bacteriophage vector, plasmid vector, or cosmid DNA; yeast containing yeast vectors; fungi containing fungal vectors; insect cell lines infected with virus (e.g. baculovirus); and mammalian cell lines transfected with plasmid or viral expression vectors, or infected with recombinant virus (e.g. vaccinia virus, adenovirus, adeno-associated virus, retrovirus, etc.).

Using methods known in the art of molecular biology, including methods described above, various promoters and enhancers can be incorporated into the vector or the DNA sequence encoding CD amino acid sequences, i.e. recombinant outer membrane protein CD, CD peptide or CD oligopeptide, to increase the expression of the CD amino acid sequences, provided that the increased expression of the CD amino acid sequences is compatible with (for example, non-toxic to) the particular host cell system used. Thus and importantly, the DNA sequence can consist of the gene encoding CD protein, or any segment of the gene which encodes a functional epitope of the CD protein. Further, the DNA can be fused to DNA encoding other antigens, such as other bacterial outer membrane proteins, or other bacterial, fungal, parasitic, or viral antigens to create a genetically fused (sharing a common peptide backbone) multivalent antigen for use as an improved vaccine composition.

The selection of the promoter will depend on the expression system used. Promoters vary in strength, i.e. ability to facilitate transcription. Generally, for the purpose of expressing a cloned gene, it is desirable to use a strong promoter in order to obtain a high level of transcription of the gene and expression into gene product. For example, bacterial, phage, or plasmid promoters known in the art from which a high level of transcription has been observed in a host cell system comprising E. coli include the lac promoter, trp promoter, recA promoter, ribosomal RNA promoter, the $P_R$ and $P_L$ promoters, lacUV5, ompF, bla, lpp, and the like, may be used to provide transcription of the inserted DNA sequence encoding CD amino acid sequences.

Additionally, if CD protein, CD peptides, or CD oligopeptides may be lethal or detrimental to the host cells, the host cell strain/line and expression vectors may be chosen such that the action of the promoter is inhibited until specifically induced. For example, in certain operons the addition of specific inducers is necessary for efficient transcription of the inserted DNA (e.g., the lac operon is induced by the addition of lactose or isopropylthio-beta-D-galactoside). A variety of operons such as the trp operon, are under different control mechanisms. The trp operon is induced when tryptophan is absent in the growth media. The $P_L$ promoter can be induced by an increase in temperature of host cells containing a temperature sensitive lambda repressor. In this way, greater than 95% of the promoter-directed transcription may be inhibited in uninduced cells. Thus expression of recombinant CD protein, CD peptides, or CD oligopeptides may be controlled by culturing transformed or transfected cells under conditions such that the promoter controlling the expression from the inserted DNA encoding CD amino acid sequences is not induced, and when the cells reach a suitable density in the growth medium, the promoter can be induced for expression from the inserted DNA.

Other control elements for efficient gene transcription or message translation include enhancers, and regulatory signals. Enhancer sequences are DNA elements that appear to increase transcriptional efficiency in a manner relatively independent of their position and orientation with respect to a nearby gene. Thus, depending on the host cell expression vector system used, an enhancer may be placed either upstream or downstream from the inserted DNA sequences encoding CD amino acid sequences to increase transcriptional efficiency. As illustrated previously in this embodiment, other specific regulatory sequences have been identified which may effect the expression from the gene encoding CD. These or other regulatory sites, such as transcription or translation initiation signals, can be used to regulate the expression of the gene encoding CD, or gene fragments thereof. Such regulatory elements may be inserted into DNA sequences encoding CD amino acid sequences or nearby vector DNA sequences using recombinant DNA methods described herein for insertion of DNA sequences.

Accordingly, *B. catarrhalis* nucleotide sequences containing regions encoding for CD protein, CD peptides, or CD oligopeptides can be ligated into an expression vector at a specific site in relation to the vector's promoter, control, and regulatory elements so that when the recombinant vector is introduced into the host cell, the *B. catarrhalis* CD-specific DNA sequences can be expressed in the host cell. For example, the CD-specific DNA sequences containing its own regulatory elements can be ligated into an expression vector in a relation or orientation to the vector promoter, and control elements which will allow for expression of CD amino acid sequences. The recombinant vector is then introduced into the appropriate host cells, and the host cells are selected, and screened for those cells containing the recombinant vector. Selection and screening may be accomplished by methods known in the art including detecting the expression of a marker gene (e.g., drug resistance marker) present in the plasmid, immunoscreening for production of CD-specific epitopes using antisera generated to CD-specific epitopes, and probing the DNA of the host's cells for CD-specific nucleotide sequences using one or more oligonucleotides and methods described according to Embodiment C herein.

Genetic engineering techniques may also be used to characterize, modify and/or adapt the encoded CD peptides or CD protein. For example, site-directed mutagenesis to modify an outer membrane protein fragment in regions outside the protective domains, may be desirable to increase the solubility of the subfragment to allow for easier purification. Further, genetic engineering techniques can be used to generate DNA sequences encoding a portion of the amino acid sequence of CD. For example, from the sequence disclosed as SEQ ID NO.14, it can be determined which restriction enzyme or combination of restriction enzymes may be used to generate sequences encoding CD peptides or CD oligopeptides. Restriction enzyme selection may be done so as not to destroy the immunopotency of the resultant peptide or oligopeptide. Antigenic sites of a protein may vary in size but can consist of from about 7 to about 14 amino acids. Thus, a protein the size of CD may contain many discrete antigenic sites; therefore, many partial gene sequences could encode antigenic epitopes of CD. Consequently, using for example SEQ ID NO.14 as a guide, restriction enzyme combinations may be used to generate DNA sequences, which when inserted into the appropriate vector, are capable of directing the production of CD-specific amino acid sequences (protein, peptides or oligopeptides) comprising one or more antigenic epitopes.

EMBODIMENT B

Conservation of the gene encoding CD amongst *B. catarrhalis* strains.

For the nucleotide sequences of the present invention to be useful in diagnostic assays, the gene encoding CD must be highly conserved amongst strains of *B. catarrhalis*. In addition, a highly conserved gene indicates that the protein sequence is also highly conserved. For a bacterial protein or peptide to be useful as an antigen in subunit vaccine formulations against infection caused by *B. catarrhalis*, the protein or peptide must contain epitopes that are both immunogenic, and conserved amongst strains of *B. catarrhalis*. To determine the degree of conservation of the CD gene among strains of *B. catarrhalis*, genomic DNA was purified and analyzed from 30 isolates recovered from diverse clinical and geographic sources (Table 1). Analysis involved restricting the DNA into fragments, and probing with an oligonucleotide of a sequence which includes , but is not limited to, those represented by SEQ ID NOs. 2–13.

TABLE 1

Sources of isolates of *Branhamella catarrhalis*

| Clinical Site | Number of Isolates |
|---|---|
| sputum | 15 |
| middle ear fluid[1] | 7 |
| nasopharynx | 3 |
| eye | 2 |
| adenoid | 1 |
| blood | 1 |
| ATCC[2] | 1 |

[1]Middle ear fluid was obtained by tympanocentesis.
[2]American Type Culture Collection.

The genomic DNA from 30 strains (including 25240) of *B. catarrhalis* was purified. A volume of 30 ml of brain heart infusion broth was inoculated with a single colony and incubated at 37° C. with shaking overnight. Cells were harvested by centrifugation at 2200×g for 10 minutes at 4° C. The pelleted cells were suspended in 7 ml of TE buffer (0.01M Tris, pH 8, 0.001M EDTA, pH 8.0). EDTA was added to 0.005M and SDS was added to 0.5%. The suspension was incubated at 60° for 30 minutes. Proteinase K was added to 200 µg/ml followed by incubation at 37° C. for approximately 24 hours. The sample was extracted sequentially with equal volumes of phenol, followed by phenol/ chloroform at a 1:1 ratio, followed by chloroform. A 10% volume of 3M sodium acetate (pH 5.2) was added and DNA was precipitated by the addition of cold ethanol equivalent to 80% of the volume. Genomic DNA precipitated and was removed by "spooling" with a pasteur pipette. The DNA was washed in 70% ethanol and dissolved in 0.05M tris, pH 8.0. RNase was added to a final concentration of 40 µg/ml and the sample was incubated at 37° for 30 minutes. EDTA was added to a concentration of 0.001M. The sample was extracted sequentially with phenol and chloroform and ethanol precipitated. The purified DNA was dissolved in 0.01M Tris, 0.1 mM EDTA, pH 8.0.

An aliquot equivalent to 10 µg of DNA was digested with EcoRI or PstI with a reaction volume of 0.5 ml. The resulting DNA fragments were separated by agarose gel electrophoresis and transferred to a charged nitrocellulose membrane by Southern blot. The Southern blots were probed with two oligonucleotide probes corresponding to sequences upstream and downstream of the EcoRI site within the gene encoding CD (this Eco RI site is depicted in FIG. 1). The oligonucleotides had been end-labeled with [$^{32}$P]ATP by using T4 polynucleotide kinase before use as probes. Hybridizations were carried out at 37° C. and washes were performed at 48° C. The hybridization and wash buffers were described previously (Nelson et al., supra). Autoradiography was performed at −70° C.

Figure 4:
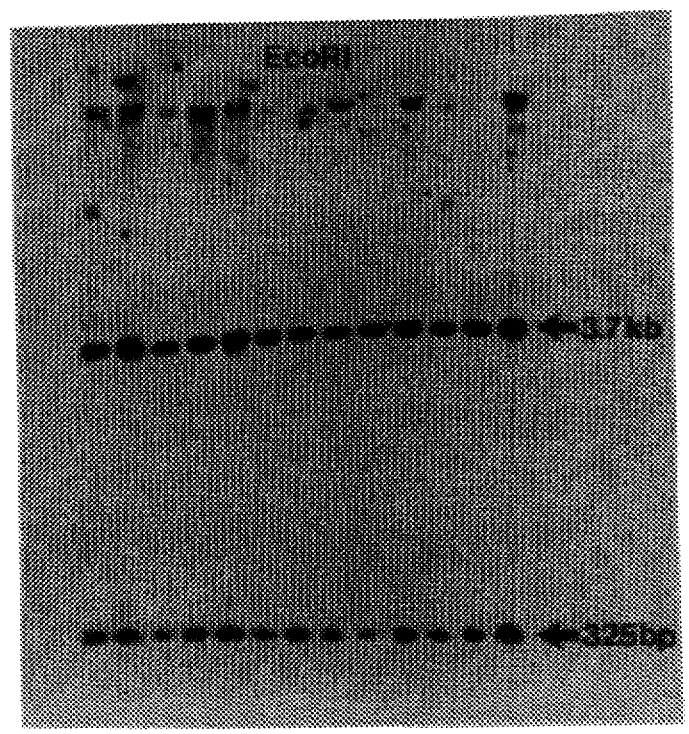
FIG. 4 represents a Southern blot assay in which purified genomic DNA of 13 strains of B. catarrhalis was cut with EcoRI and probed with two labeled oligonucleotides corresponding to CD gene sequence. The arrow denoting the 3.7 kilobase band represents a fragment upstream of the EcoRI site within the gene encoding CD and the arrow denoting the 325 base pair band represents the fragment downstream of the EcoRI site. Lanes contain DNA from the following strains from left to right: 105, 112, 135, 3, 6, 10, 20, 27, 31, 40, 42, 45, 56.

All 30 strains produced an identical pattern of bands, including a 325 bp band representing the fragment between the EcoRI site within the gene and the site just downstream of the gene. In addition, all 30 strains showed a 3.7 kb band representing a fragment upstream of the CD gene. This pattern is exemplified by FIG. 4 showing the Southern blot assay of 13 strains.

Figure 5:
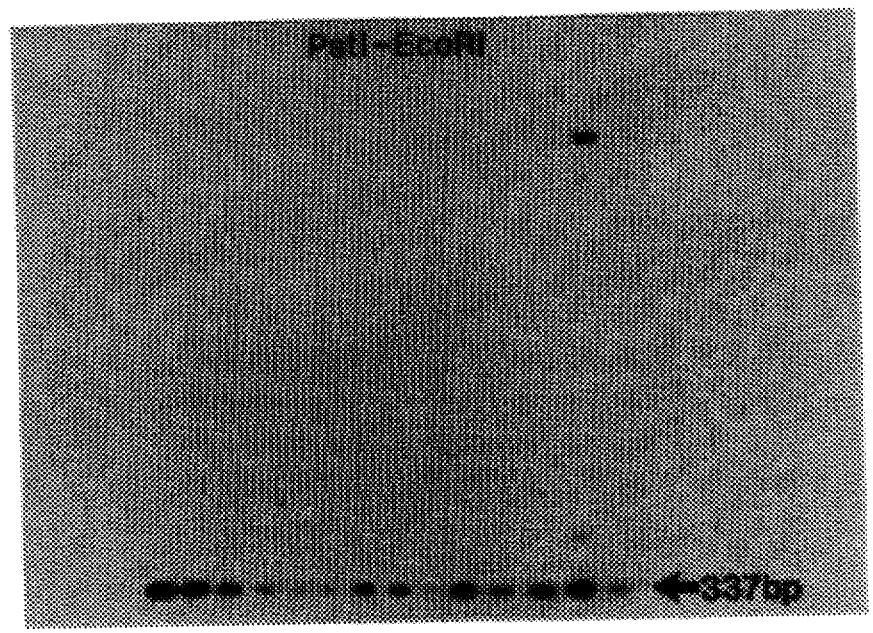
FIG. 5 represents a Southern blot assay in which purified genomic DNA of 14 strains of B. catarrhalis was cut with EcoRI and PstI and probed with a labeled oligonucleotide corresponding to sequence between the EcoRI and PstI sites within the gene encoding CD. Lanes contain DNA from the following strains from left to right: 555, 556, 585, 3583, 3614, 4223, 4629, 5193, 6951, 9928, 25240, M3, M3, M9.

To further analyze the molecular conservation of the CD gene, genomic DNA from the same 30 strains was digested with EcoRI and PstI and probed with oligonucleotides. FIG. 1 shows that the gene encoding CD, isolated from strain 25240, has a PstI site near the center of the gene and that digestion with EcoRI and PstI will yield a DNA fragment of 337 base pairs. Southern blot assays showed that genomic DNA from 30 of 30 strains of *B. catarrhalis* yielded an identical 337 bp fragment which hybridized with an oligonucleotide corresponding to sequence in the gene encoding CD isolated from strain 25240. This pattern is exemplified by FIG. 5 showing the Southern blot assay of 13 strains. These findings indicate that the gene encoding CD is highly conserved amongst strains of *B.catarrhalis*, and therefore the nucleotide sequences described herein have applications for diagnostic and vaccine use.

EMBODIMENT C

Methods for using CD-specific nucleotide sequences in molecular diagnostic assays for the detection of *B. catarrhalis*.

Because of the conservation of the gene encoding CD, as disclosed in Embodiment B, the nucleic acid sequences of the present invention can be used in molecular diagnostic assays for detecting *B. catarrhalis* genetic material. In particular, CD sequence-specific oligonucleotides can be synthesized for use as primers and/or probes in amplifying, and detecting amplified, nucleic acids from *B. catarrhalis*. Recent advances in molecular biology have provided several means for enzymatically amplifying nucleic acid sequences. Currently the most commonly used method, PCR™ (polymerase chain reaction, Cetus Corporation) involves the use of Taq Polymerase, known sequences as primers, and heating cycles which separate the replicating deoxyribonucleic acid (DNA) strands and exponentially amplify a gene of interest. Other amplification methods currently under development include LCR™ (ligase chain reaction, BioTechnica International) which utilizes DNA ligase, and a probe consisting of two halves of a DNA segment that is complementary to the sequence of the DNA to be amplified; enzyme QB replicase (Gene-Trak Systems) and a ribonucleic acid (RNA) sequence template attached to a probe complementary to the DNA to be copied which is used to make a DNA template for exponential production of complementary RNA; and NASBA™ (nucleic acid sequence-based amplification, Cangene Corporation) which can be performed on RNA or DNA as the nucleic acid sequence to be amplified.

Nucleic acid probes that are capable of hybridization with specific gene sequences have been used successfully to detect specific pathogens in biological specimens at levels of sensitivity approaching $10^3-10^4$ organisms per specimen (1990, *Gene Probes for Bacteria*, eds. Macario and deMacario, Academic Press). Coupled with a method that allows for amplification of specific target DNA sequences, species-specific nucleic acid probes can greatly increase the level of sensitivity in detecting organisms in a clinical specimen. Use of these probes may allow direct detection without relying on prior culture and/or conventional biochemical identification techniques. This embodiment of the present invention is directed to primers which amplify species-specific sequences of the gene encoding CD of *B. catarrhalis*, and to probes which specifically hybridize with these amplified DNA fragments. By using the nucleic acid sequences of the present invention and according to the methods of the present invention, as few as one *B. catarrhalis* organism may be detected in the presence of 10 µg/ml extraneous DNA.

This embodiment is directed to species-specific oligonucleotides which can be used to amplify sequences of *B. catarrhalis* DNA, if present, from DNA extracted from clinical specimens including middle ear fluid, sputum, blood, and fluids from the nasopharynx, eye, and adenoid; and to subsequently determine if amplification has occurred. In one embodiment of the present invention, a pair of *B. catarrhalis*-specific DNA oligonucleotide primers are used to hybridize to *B. catarrhalis* genomic DNA that may be present in DNA extracted from a clinical specimen, and to amplify the specific segment of genomic DNA between the two flanking primers using enzymatic synthesis and temperature cycling. Each pair of primers are designed to hybridize only to the *B. catarrhalis* nucleotide sequences of the present invention to which they have been synthesized to complement; one to each strand of the double-stranded DNA. Thus, the reaction is specific even in the presence of microgram quantities of heterologous DNA. For the purposes of this description, the primer derived from the sequence of the positive (gene) strand of DNA will be referred to as the "positive primer", and the primer derived from the sequence of the negative (complementary) strand will be referred to as the "negative primer".

Amplification of DNA may be accomplished by any one of the methods commercially available. For example, the polymerase chain reaction may be used to amplify the DNA. Once the primers have hybridized to opposite strands of the target DNA, the temperature is raised to permit replication of the specific segment of DNA across the region between the two primers by a thermostable DNA polymerase. Then the reaction is thermocycled so that at each cycle the amount of DNA representing the sequences between the two primers is doubled, and specific amplification of the *B. catarrhalis* DNA sequences, if present, results. Further identification of the amplified DNA fragment, as being derived from *B. catarrhalis* DNA, may be accomplished by liquid hybridization. This test utilizes one or more labeled oligonucleotides as probes to specifically hybridize to the amplified segment of *B. catarrhalis* DNA. Detection of the presence of sequence-specific amplified DNA may be accomplished using any one of several methods known in the art such as a gel retardation assay with autoradiography. Thus, the nucleotide sequences of the present invention provide basis for the synthesis of oligonucleotides which have commercial applications in diagnostic kits for the detection of *B. catarrhalis*. In a related embodiment, the oligonucleotides used as primers may be labeled directly, or synthesized to incorporate label. Depending on the label used, the amplification products can then be detected, after binding onto an affinity matrix, using isotopic or colorimetric detection.

DNA may be extracted from a clinical specimens which may contain *B. catarrhalis* using methods known in the art. For example, cells contained in the specimen may be washed in TE buffer and pelleted by centrifugation. The cells then may be resuspended in 100 µl of amplification reaction buffer containing detergents and proteinase K. Using the polymerase chain reaction, the resultant sample may be composed of the cells in 10 mM Tris pH 8.3, 50 mM KCl, 1.5 mM $MgCl_2$, 0.01% gelatin, 0.45% (NP40™), 0.045% non-ionic detergent (Tween 20™), and 60 µg/ml proteinase K. The sample is incubated at 55° C. water bath for 1 hour. Following the incubation, the sample is incubated at 95° C. for 10 minutes to heat-inactivate the proteinase K. The sample may then be amplified in accordance with the protocol for the polymerase chain reaction as set forth below.

The *B. catarrhalis* DNA may be amplified using any one of several protocols for amplifying nucleic acids by the polymerase chain reaction. In one mode of this embodiment, the gene encoding CD was amplified from 25 clinical isolates of *B. catarrhalis* using the following conditions.

DNA to be amplified (≈1 μg of genomic DNA) was distributed in 0.5 ml microfuge tubes and the volume was adjusted to 50 μl by adding a reaction mixture comprising 0.2 mM dNTPs (dATP, dCTP, dGTP, dTTP), 0.25 μg of each positive and negative oligonucleotide primer, 1 unit of TaqI polymerase, TaqI 10×buffer (5 μl), 1 mM $MgCl_2$ (final concentration), and sterile distilled water to achieve the total volume. The TaqI polymerase is added to the reaction mixture just before use and is gently mixed, not vortexed. A layer of mineral oil, approximately 2 drops, is added to each tube and then the tubes are placed in the thermal cycler. Thirty to thirty-five cycles are generally sufficient for bacterial DNA amplification. One cycle consists of 1 minute at 95° C., 1 minute at 37° C., and 1 minute at 72° C. The first cycle includes a 1½ minute incubation at 95° C. to assure complete denaturation.

Oligonucleotides useful as primers or probes which specifically hybridize to the gene encoding CD of *B. catarrhalis* and used in DNA amplification and/or detection can be biochemically synthesized, using methods known in the art, from the nucleotide sequences disclosed in the present invention. The specificity of the oligonucleotides for *B. catarrhalis* can be checked by a gene-bank database (Genbank) search for each individual sequence. In general, the oligonucleotides should be selected for low G-C content. Pairs of primers that have been used for this embodiment to amplify the whole gene encoding CD include SEQ ID NO. 15 (negative primer) and SEQ ID NO. 16 (positive primer). Pairs of primers used to amplify the portion of the gene that encodes 5E8 and 7D6 epitopes include SEQ ID NO. 17 (negative primer) and SEQ ID NO. 18 (positive primer).

For detection purposes, the oligonucleotides of the present invention may be end-labeled with a radioisotope. Probe sequences, internal to the two primers used for amplification of the gene sequence, may be end-labeled using $T_4$ polynucleotide kinase and gamma $^{32}P$ ATP. Twenty pMols of probe DNA in kinase buffer (50 mM Tris, pH 7.6, 10 mM $MgCl_2$, 5 mM dithiothreitol, 0.1 mM spermidine-HCl, 0.1 mM EDTA, pH 8.0) is mixed with 120 μCi of gamma $^{32}P$ ATP and incubated at 37° C. for 1 hour. Labeled probe is separated from unincorporated label on an 8% acrylamide gel run for 1 hour at 200 volts in Tris Borate EDTA (TBE) buffer at room temperature. Labeled probe is first located by exposing the acrylamide gel to x-ray film for three minutes. The resulting autoradiogram is then positioned under the gel, and the band containing the labeled probe was excised from the gel. The gel slice is pulverized in one milliliter of sterile distilled water, and the probe is eluted by shaker incubation overnight at 37° C. The eluted probe is separated from the gel fragments by centrifugation using a chromatography prep column. Radioactivity of the probe is determined, by counting one microliter of the labeled probe on a glass fiber filter, by liquid scintillation. Such probe sequences may be chosen from any of the sequences identified as SEQ ID NOs. 2–13 provided the probe sequence is internal to the two primers used for amplification of the desired nucleotide sequence disclosed in the present invention.

Alternative methods known in the art may be used to improve the detection of amplified target sequences in accordance with the compositions and methods of the present invention. The sensitivity of detection of the amplified DNA sequences can be improved by subjecting the sequences to liquid hybridization. Alternative methods of detection known in the art, in addition to gel electrophoresis and gel electrophoresis with Southern hybridization and autoradiography, that may be used with the compositions and methods of the present invention include: restriction enzyme digestion with gel electrophoresis; slot-blot hybridization with a labeled oligonucleotide probe; amplification with a radiolabeled primer with gel electrophoresis, Southern hybridization and autoradiography; amplification with a radiolabeled primer with dot blot and autoradiography; amplification with oligonucleotides containing affinity tags (ex. biotin, or one primer incorporating biotin and the other primer with a sequence specific for a DNA binding protein) followed by detection in an affinity-based assay (ex. ELISA); and amplification with oligonucleotides containing fluorophores followed by fluorescence detection.

One embodiment of non-isotopic detection involves incorporating biotin into the oligonucleotide primers of the present invention. The 5'-aminogroup of the primers may be biotinylated with sulfo-NHS-biotin, or biotin may be incorporated directly into the primer by synthesizing the primer in the presence of biotin-labeled dNTPs. The non-isotopic labeled primers are then used in amplifying DNA from a clinical specimen. The detection for the presence or absence of amplified target sequences may be accomplished by capturing the amplified target sequences using an affinity matrix having avidin bound thereto, followed by incubation with an avidin conjugate containing an enzyme which can be used to visualize the complex with subsequent substrate development. Alternately, the amplified target sequences may be immobilized by hybridization to the corresponding probes of the target sequence wherein the probes have been affixed onto a matrix. Detection may be accomplished using an avidin conjugate containing an enzyme which can be used to visualize the complex with subsequent substrate development.

EMBODIMENT D

Characterization of CD, including generation of CD peptides.

To confirm that the gene encoding CD had been identified, the amino terminus of the CD protein was determined. To identify the amino terminus of the CD protein, purified outer membrane of *B. catarrhalis* 25240 was subjected to SDS-PAGE and transferred to polyvinylidine difluoride membrane by electrophoretic blotting. The CD band was excised and the amino terminal sequence of the protein was determined by Edmund degradation, with the amino acids being analyzed by a microsequencer. The amino terminal sequence, G-V-T-V-S-P-L-L-L-G corresponded to amino acids 27 through 36 of the open reading frame of pCD1, indicating that CD has a 26 amino acid leader peptide. A hydrophobic 26 amino acid leader peptide is characteristic of bacterial OMPs whose leader peptides are cleaved by signal peptidase I (Oliver, 1985, *Ann. Rev. Microbiol.* 39:615–648).

To further establish that the gene encoding CD had been identified, the amino acid sequence deduced from the gene sequence was analyzed for the presence of methionine residues to predict the result of cyanogen bromide cleavage of the protein. The open reading frame corresponding to the mature protein contains four methionines indicating that cleavage with cyanogen bromide would yield five fragments. Cyanogen bromide cleavage of CD was accomplished by purifying outer membrane (Murphy et al., 1989, *Infect. Immun.* 57:2938–2941) and subjecting the outer membrane preparation to SDS-PAGE. The gel was stained with amido black so that the CD band could be visualized and excised from the gel. The gel slices (3–4 mm in length) were placed into the tubes of an electroeluter with 0.05M ammonium bicarbonate, 0.1% SDS. The protein was eluted, at 10 mA per tube until the gel slices were completely free of amido black (approximately 5 hours). The eluted protein was collected and an aliquot of 0.6 ml was precipitated by the addition of 2 ml of cold ethanol. The sample was centrifuged and the pellet was air dried. A volume of 0.4 ml of cyanogen bromide (200 mg/ml) in 70% formic acid was added to the pellet and the sample was incubated overnight at room temperature in the dark. A simultaneous control sample was incubated in 70% formic acid under identical conditions. The next day 1 ml of water was added and the samples were lyophilized. The lyophilized peptides were suspended in sample buffer and subjected to tricine gel electrophoresis.

Figure 6:
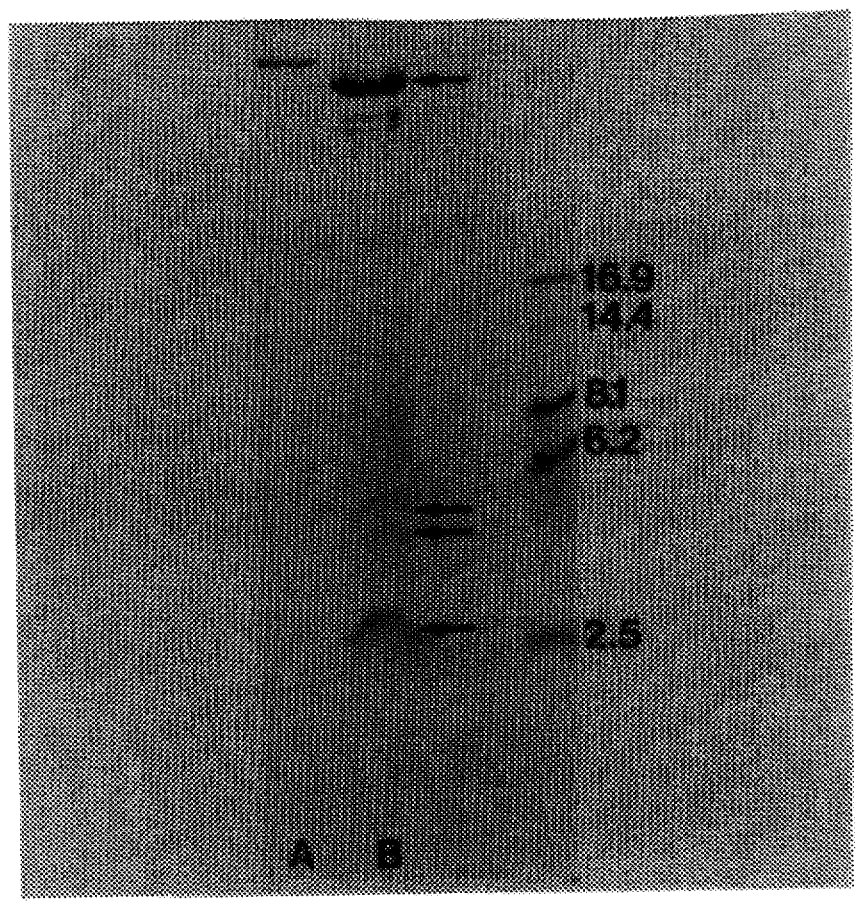
FIG. 6 represents a tricine-sodium docecyl sulfate gel stained with Coomassie blue. Lane A: purified CD. Lane B: Purified CD cleaved with cyanogen bromide. The arrows denote the fragments resulting from cyanogen bromide cleavage (calculated sizes of these fragments appear in Table 2). The double band below the large fragment in lane B is a result of nonspecific proteolytic breakdown of the protein which is frequently observed with CD. Molecular mass markers are noted on the right in thousands of daltons.

Table 2 shows the size of the fragments (CD peptides) predicted by the methionine sites in the open reading frame. FIG. 6 shows the actual fragments obtained from cyanogen bromide treatment of purified CD, as determined by the tricine polyacrylamide gel system of Lesse et al. (1990, *J. Immunol. Methods* 126:109–117). The predicted and actual sizes of the cyanogen bromide cleaved fragments are in good agreement with the exception of the large fragment from the amino terminal region of the protein (Table 2).

TABLE 2

Cyanogen bromide cleavage fragments of outer membrane protein CD of *Branhamella catarrhalis*

| Molecular mass[1] predicted from gene sequence[2] | Molecular mass measured from SDS-PAGE[3] |
|---|---|
| 34,919 | ~50,000 |
| 4,408 | 4,900 |
| 3,593 | 4,000 |
| 2,450 | 2,500 |
| 358 | |

[1]Molecular masses are noted in daltons.
[2]See SEQ ID No. 14 for nucleotide sequence.
[3]SDS-PAGE: Sodium dodecyl sulfate polyacrylamide gel electrophoresis. See FIG. 6 for tricine gels.

Thus, the open reading frame identified in pCD1 represents the entire gene encoding CD and the protein behaves aberrantly in SDS-PAGE. This discrepancy between the predicted molecular mass and the molecular mass observed in SDS-PAGE appears to be due to a proline-rich region in the large cyanogen bromide fragment in the amino terminal region of the protein as a variety of other proline-rich proteins demonstrate this characteristic (Postle et al., 1983, *Proc. Natl. Acad. Sci. U.S.A.* 50:5235–5239; Woods et al., 1989, *Mol. Microbiol.* 3(1):43–48; and Thole et al., 1990, *Infect. Immun.* 58:80–87).

A search of sequence data bases disclosed that the sequence of the CD gene shares homology with the OprF genes of *Pseudomonas* species. The CD protein contains a region (amino acid 240–280) which is rich in proline, alanine and valine. This sequence shares homology with the TonB protein of *E. coli* and *Serratia marcescens*.

EMBODIMENT E

Methods for using CD, or CD peptides, in diagnostic immunoassays.

CD protein, CD peptides, and CD oligopeptides can be purified for use as immunogens in vaccine formulations; and as antigens for diagnostic assays or for generating *B. catarrhalis* specific antisera of therapeutic and/or diagnostic value. CD protein from *B. catarrhalis* or oligopeptides or peptides thereof, or recombinant CD protein, recombinant CD peptides, or recombinant CD oligopeptides produced from an expression vector system, can be purified with methods known in the art including detergent extraction, chromatography (e.g., ion exchange, affinity, immunoaffinity, or sizing columns), differential centrifugation, differential solubility, or other standard techniques for the purification of proteins.

1) For example, a partially purified preparation, containing primarily bacterial outer membrane proteins, can be prepared as follows. *B. catarrhalis* cultures from 30 chocolate agar plates were scraped into 25 ml of PBS, pH 7.2, and harvested by centrifugation at 12,000×g for 20 minutes at 4° C. The bacterial pellet was resuspended in 10 ml of 1M sodium acetate-0.001M β-mercaptoethanol (pH 4.0). A 90-ml volume of a solution containing 5% Zwitterionic detergent (ZWITTERGENT™ Z 3-14) (Calbiochem-Behring) and 0.5% M CaCl$_2$ was added, and the suspension was mixed for 1 hour at room temperature. Nucleic acids were precipitated by the addition of 25 ml cold ethanol and subsequent centrifugation at 17,000×g for 10 minutes at 4° C. The remaining proteins were precipitated by the addition of 375 ml cold ethanol and collected by centrifugation at 17,000×g for 20 minutes at 4° C. The pellets were allowed to dry and were then suspended in 10 ml of detergent buffer containing 0.05% Zwitterionic detergent (Zwittergent) 0.05M Tris, 0.01M EDTA, pH 8.0, and mixed for 1 hour at room temperature. The bacterial outer membrane proteins are present in the soluble fraction of the detergent buffer after centrifugation at 12,000×g for 10 minutes at 4° C.

Immunopurification of the CD protein from an outer membrane protein preparation may be accomplished using methods known in the art for immunoaffinity chromatography. CD-specific monoclonal antibodies, such as 5E8 and 7D6, may be linked to a chromato- graphic matrix to form an affinity matrix. The outer membrane protein preparation is then incubated with the affinity matrix allowing the antibodies to bind to CD. The affinity matrix is then washed to remove unbound components and CD is then eluted from the affinity matrix resulting in a purified preparation of CD protein. The purified CD may be used as an antigen for diagnostic assays, or may be chemically or enzymatically cleaved into peptides, as illustrated in Embodiment D. Alternatively, CD peptides may be synthesized using the deduced amino acid sequence from the gene encoding CD as a reference.

2) In another illustration of this embodiment, recombinant CD was purified from a polyhistidine expression plasmid. To purify recombinant CD by this method, the gene encoding CD was cloned into a polyhistidine expression vector such as plasmid pRSETA (Invitrogen Corporation), such that upon expression several histidine residues ("polyhistidine tail") are attached to the amino terminus of the CD protein. A BamHI fragment containing the gene encoding CD was ligated into the expression vector which had been previously restricted with BamHI and subsequently treated with calf intestinal phosphatase. The ligation mixture was used to electroporate *E. coli* strain BL21(DE3) cells, and transformants were analyzed for recombinant plasmids containing the gene encoding CD in the proper orientation with respect to the plasmid promoter. One such clone, termed pCDSA, was isolated and was also shown to express CD protein when introduced into the *E. coli* host strain.

Recombinant CD was purified as follows. A 15 ml volume of a culture of transformants containing pCDSA was grown overnight in LB ampicillin broth at 37° C. The following morning, 135 ml of broth was inoculated with the overnight culture and grown for 1 hour at 37° C. Cells were recovered by centrifugation at 5,000×g for 10 minutes at 4° C. Cells were resuspended in 10 ml of guanidinium lysis buffer (6M guanidine hydroxide, 20 mM sodium phosphate, 500 mM sodium chloride, pH 7.8). The suspension was mixed for 10 minutes at room temperature. Cells were then sonicated with 3 bursts of 5 seconds each using a sonifier at the #4 setting. The mixture was centrifuged at 3,000×g for 15 minutes at 4° C. and the supernatant was saved. The supernatant was then mixed for 10 minutes at room temperature with 1.6 ml of a resin (e.g., ProBond™, Invitrogen) which, via nickel on the resin, binds to the polyhistidine tail of the recombinant CD protein. The resin was then isolated by centrifugation.

CD protein was eluted from the resin by first washing the resin twice with 4 ml of denaturing wash buffer (8M urea, 20 mM sodium phosphate, 500 mM sodium chloride, pH 7.8). The resin was then washed 2 times with 4 ml volumes of denaturing wash buffer at pH 6.0. This was followed by washing the column twice with 4 ml volumes of denaturing wash buffer at pH 4.0. Fractions of 1 ml each were collected and dialyzed against phosphate-buffered saline (PBS) containing a detergent (0.1% Triton™ X-100). Analysis of the eluted CD protein by gel electrophoresis and Coomassie blue staining revealed a single band. It is estimated that this method results in a preparation of CD protein which is 95% purified. The resultant purified recombinant CD protein is immunoreactive with monoclonal antibodies which recognize native CD protein.

3) In another illustration of this embodiment, native CD protein was purified from *B. catarrhalis*. *B. catarrhalis* isolate O35E was grown in Mueller-Hinton broth for 24 hours at 36° C. The bacteria were then harvested by centrifugation at 4,000×g for 20 minutes. The bacterial pellets were suspended in pH 7.0 buffer containing 0.01M phosphate and 0.64M sodium chloride. The resuspended bacteria were vortexed vigorously for 2 minutes, and then centrifuged at 30,000×g for 20 minutes. The supernatant, containing outer membrane vesicles, was saved and dialyzed against a solution containing 10 mM Tris, 10 mM NaCl and 1 mM EDTA. After dialysis, a detergent (Triton™ X-100) was added to a concentration of 1.0%, and the dialysate was then incubated for 1 hour at room temperature to solubilize the proteins. Insoluble material was removed by centrifugation at 10,000×g for 10 minutes. The supernatant was loaded onto an ion exchange column. The column was washed with a buffer of 10 mM Tris, 1% TRITON™ X-100 (pH 8.0) and the protein eluted with the buffer containing either 50 mM NaCl or 100 mM NaCl. Subsequent passage of the eluted protein preparation over a gel filtration column, that had been equilibrated with the buffer, yielded preparations of protein that were free of other detectable proteins by Coomassie Brilliant Blue staining of SDS-PAGE gels, and free of lipooligosaccharides by silver staining of SDS-PAGE gels.

4) As used throughout the specification, CD oligopeptides are defined herein as a series of peptides corresponding to a portion of the amino acid sequence of CD protein as disclosed in SEQ ID NO.14 that are synthesized as one or chemically-linked. Such peptides or oligopeptides can be synthesized using one of the several methods of peptide synthesis known in the art including standard solid peptide synthesis using tert-butyloxycarbonyl amino acids (Mitchell et al., 1978, *J. Org. Chem.* 43:2845–2852), using 9-fluorenylmethyloxycarbonyl amino acids on a polyamide support (Dryland et al., 1986, *J. Chem. So. Perkin Trans. I*, 125–137); by pepscan synthesis (Geysen et al., 1987, *J. Immunol. Methods* 03:259; 1984, *Proc. Natl. Acad. Sci. U.S.A.* 81:3998); by standard liquid phase peptide synthesis; or by recombinant expression vector systems. Modification of the peptides or oligopeptides, such as by deletion and substitution of amino acids (and including extensions and additions to amino acids) and in other ways, may be made so as to not substantially detract from the immunological properties of the peptide or oligopeptide. In particular, the amino acid sequence of the CD protein, or peptide or oligopeptide thereof, may be altered by replacing one or more amino acids with functionally equivalent amino acids resulting in an alteration which is silent in terms of an observed difference in the physicochemical behavior of the protein, peptide, or oligopeptide. Functionally equivalent amino acids are known in the art as amino acids which are related and/or have similar polarity or charge. Thus, an amino acid sequence which is substantially that of the amino acid sequences depicted in the Sequence Listing herein, refers to an amino acid sequence that contains substitutions with functionally equivalent amino acids without changing the primary biological function of protein, peptide, or oligopeptide.

5) In an illustration of production of CD peptides containing epitopes of CD, defined regions of the CD protein were expressed in an expression system wherein the plasmid expression vector (pGEX2T) directs the synthesis of foreign polypeptides in *E. coli* as a fusion peptides with glutathione-S-transferase (GST), a 26 kilodalton protein from *Schistosoma japonicum*. In this mode of the embodiment, and using pCD2 as the template, selected regions of the gene encoding CD was amplified by the polymerase chain reaction using oligonucleotides corresponding to sequences shown in Table 3. Table 3 also shows the amino acid positions of the peptides, relative to the mature CD protein as illustrated in SEQ ID NO.14, as encoded by the peptide constructs. The oligonucleotides were designed so that the resulting amplified gene fragment contained a BamH1 restriction site on its 5' end, and an EcoR1 restriction site on the 3' end so that the amplified fragment could be directionally cloned into pGEX2T. The sequence of each recombinant plasmid was confirmed by dideoxy sequencing. To purify each recombinant CD peptide, the respective recombinant plasmid containing the gene fragment was transformed into *E. coli* JM109. The transformant was grown in 400 ml of LB broth containing 25 µg/ml of ampicillin by adding forty ml of an overnight culture to 360 ml of broth, and incubating for 1.5 hours at 37° C. with shaking. IPTG was added to 0.01 mM and the culture was incubated for an additional 3 hours. Cells were centrifuged at 5000×g and the cell pellet was resuspended in 5 ml of PBS. Cells were sonicated and the mixture was centrifuged at 10,000×g for 10 minutes. The supernatant was mixed with 0.5 ml of pre-swelled glutathione-agarose beads. After mixing for 2 minutes at room temperature, the beads (with fusion peptide bound to the glutathione) were washed 2 additional times with PBS containing 1% non-ionic detergent (TRITON™ X-100). The beads were then washed once in 0.05M Tris, pH 8.0. To cleave the CD peptide from the glutathione-S-transferase, the washed beads were incubated in 0.25% (final concentration) human thrombin in Tris buffer for 1 hour at room temperature. A protease inhibitor, phenylmethylsulfonylfluoride PMSF, was then added to a concentration of 100 µg/ml. The beads were removed by centrifugation and the supernatant contained purified CD peptide. Immunoblot assays affirmed that the fusion peptides were immunoreactive, though at varying degrees with CD-specific rabbit polyclonal antiserum.

TABLE 3

| Clone | Amino Acid positions | Oligonucleotides |
|---|---|---|
| Px1 | 1–105 (SEQ ID NO. 19) | SEQ ID NOs. 20–21 |
| Px106 | 106–202 (SEQ ID NO. 22) | SEQ ID NOs. 23–24 |
| Px203 | 203–261 (SEQ ID NO. 25) | SEQ ID NOs. 26–27 |
| Px261L | 261–331 (SEQ ID NO. 28) | SEQ ID NOs. 29–30 |
| Px261 | 261–301 (SEQ ID NO. 31) | SEQ ID NOs. 29 & 32 |
| Px286L | 286–311 (SEQ ID NO. 33) | SEQ ID NOs. 34–35 |
| Px286 | 286–301 (SEQ ID NO. 36) | SEQ ID NOs. 34 & 37 |
| Px293 | 293–303 (SEQ ID NO. 38) | SEQ ID NOs. 39–40 |
| Px295 | 295–311 (SEQ ID NO. 41) | SEQ ID NOs. 42–43 |
| Px311 | 311–331 (SEQ ID NO. 44) | SEQ ID NOs. 45–46 |
| Px332 | 332–390 (SEQ ID NO. 47) | SEQ ID NOs. 48–49 |
| Px391 | 391–427 (SEQ ID NO. 50) | SEQ ID NOs. 51–52 |

Purified CD protein, CD peptides, and CD oligopeptides may be used as antigens in immunoassays for the detection of *Branhamella catarrhalis*-specific antisera present in the body fluid of an individual suspected of having an infection caused by *B. catarrhalis*. The body fluids include, but are not limited to, middle ear fluid, sputum, blood, and fluids from the nasopharynx, eye, and adenold. The detection of CD or CD peptides as an antigen in immunoassays, includes any immunoassay known in the art including, but not limited to, radioimmunoassay, enzyme-linked immunosorbent assay (ELISA), "sandwich" assay, precipitin reaction, agglutination assay, fluorescent immunoassay, and chemiluminescence-based immunoassay.

EMBODIMENT F

Methods and compounds for vaccine formulations related to CD and peptides.

This embodiment of the present invention is to provide CD protein and/or peptides or oligopeptides thereof, to be used in as immunogens in a prophylactic and/or therapeutic vaccine for active immunization to protect against or treat infections caused by *B. catarrhalis*. For vaccine purposes, an antigen of *B. catarrhalis* comprising a bacterial protein should be immunogenic, and induce functional antibodies directed to one or more surface-exposed epitopes on intact bacteria, wherein the epitope(s) are conserved amongst strains of *B. catarrhalis*.

In one illustration of the CD protein having the properties desirable of a vaccine antigen, the protein was purified from *B. catarrhalis* using the method described herein in Embodiment E, Example 3. Mice were immunized with the purified CD protein (25 µg) with adjuvant (20 µg of QS21) two times at four week intervals. Blood from the immunized mice was drawn 32 days after the last immunization and the immune sera was pooled. The pooled immune sera was assayed against whole bacteria (*B. catarrhalis* strain O35E) by an enzyme linked immunosorbent assay (ELISA). For the whole cell ELISA, overnight cultures of bacteria were harvested by a swab and suspended in PBS to an absorbance of 0.1 at 600 nm. Aliquots (100 µl) of the bacterial suspension were added to the wells of a 96 well microtiter plate and dried overnight at room temperature. The plates were blocked with 100 µl of 0.1% (w/v) gelatin in PBS. This, and all remaining incubations, were for one hour at room temperature unless otherwise specified. The blocking solution was removed and 100 µl of the immune sera, diluted in PBS with 0.1% (w/v) gelatin, was added to the wells and incubated. After washing three times with PBS, the bound antibodies were detected by incubating with 100 µl of alkaline phosphatase conjugated recombinant protein G (1:1500 in PBS with 0.1% (w/v) gelatin). The plates were washed and color development was facilitated by the addition of 100 µl/well of p-nitrophenyl phosphate (2 mg/ml in diethanolamine). After 30 minutes, the reaction was stopped by adding 50 µl of 3M NaOH. The absorbance was read at 492 nm using an ELISA reader. Endpoint titers were determined as the reciprocal of the dilution at which the absorbance was greater than that of the blank wells. The results, given in Table 4, demonstrate that immunization with CD protein can elicit antibodies which can bind to one or more surface-exposed epitopes on intact *B. catarrhalis*.

TABLE 4

| Titer of serum against strain O35E | |
|---|---|
| Serum | Endpoint titer |
| pre-immune control | <50 |
| immune (anti-CD) sera | 7,800 |

Additional evidence supporting the immunogenicity of the CD protein comes from a study of the human immune response to outer membrane proteins of *B. catarrhalis*, in which 11 of 13 patients with well-documented infections caused by *B. catarrhalis* had IgG to CD in their convalescent sera (unpublished). The 13 patients included 6 children with otitis media and 7 adults with bronchopulmonary infections due to *B. catarrhalis*.

In another illustration that the CD protein possesses properties desirable of a vaccine antigen, it was demonstrated that CD protein is the target of bactericidal antibody generated from immunization with CD protein. For example, polyclonal antiserum to CD protein was raised in a rabbit by immunizing with CD protein subcutaneously. Outer membrane preparations of *B. catarrhalis* were subjected to SDS-PAGE, and bands in the gel corresponding to CD were cut out, and then CD protein was purified by elution from the polyacrylamide gel slices. A rabbit was immunized at day 0 with 40 µg of CD protein in incomplete Freund's adjuvant, day 14 with 90 µg of CD protein in incomplete Freund's adjuvant, and day 28 with 60 µg of CD protein in incomplete Freund's adjuvant. The resultant antiserum was tested for its bactericidal activity against strain 4223NC of *B. catarrhalis*. The bacteria were grown to logarithmic phase in brain-heart infusion (BHI) broth. An aliquot of the bacterial culture was diluted to $5 \times 10^4$ colony forming units (CFU) per ml in 10% bovine serum albumin in a balanced salt solution. The bactericidal assay reaction contained bacteria, polyclonal antiserum to CD protein, a complement source consisting of normal human serum which was absorbed with protein G to remove antibodies, and the balanced salt solution. All reagents were added to the reaction to yield a 250 µl volume. Aliquots of 25 µl of the reaction were removed and plated in triplicate on BHI agar at times 0 and 60 minutes. The plates were incubated and colonies were counted the next day. The percent killing was calculated using the average of the three triplicate values at the 2 times. A representative example of data generated by the bactericidal assays is shown in Table 5. The results indicate that the polyclonal antiserum raised to CD protein is bactericidal for *B. catarrhalis*. As illustrated by Table 5, controls show that the antiserum does not kill bacteria in the absence of complement, and that the complement source does not kill the bacteria in the absence of the antiserum, indicating that the bactericidal activity is antibody directed and complement mediated.

TABLE 5

Bactericidal activity of anti-CD antibody

| Sample | Antiserum | Complement | CFU at time 0 | CFU at time 60 | percent killing |
|--------|-----------|------------|---------------|----------------|-----------------|
| 1 | 10 μl | 22 μl | 225 | 5 | 97.8% |
| 2 | 10 μl | 0 | 227 | 390 | 0% |
| 3 | 0 | 22 μl | 254 | 286 | 0% |

In further illustrating that CD protein possesses properties desirable of a vaccine antigen, pooled immune sera raised to strain O35E was shown to have cross-reactivity with heterologous strains. The pooled immune sera, prepared against CD protein as described above, was examined for cross-reactivity with nine B. catarrhalis strains from diverse clinical and geographical sources. These include strains isolated from clinical sources such as middle ear and from the upper respiratory tract, and from geographical sources such as New York state, Massachusetts, and Tennessee. The assay was performed by culturing the strains overnight on Mueller-Hinton agar. Bacteria from each culture were harvested by swabs and suspended in PBS to an optical absorbance of 1.0 at 600 nm. A microliter of each suspension was applied to a nitrocellulose membrane and allowed to dry. The membrane was incubated one hour at room temperature in a solution of 5% non-fat dry milk in PBS to block the residual binding sites of the membrane. The membrane was washed twice with PBS, and then immersed in the blocking solution containing the immune sera diluted to 1:1000. The membrane was incubated with the antibody overnight at 4° C. with gentle shaking. The membrane was washed three times with PBS and then incubated for 2 hours at room temperature with alkaline phosphatase conjugated recombinant protein G (1:1500 in PBS with 5% non-fat dry milk). The membrane was washed three times with PBS and bound antibody was detected by the addition of substrate (KPI BCIP/NBT phosphatase substrate system; Kirkegaard and Perry, Inc.). The immune sera reacted with six strains as strongly, or to a greater extent than, strain O35E; while the immune sera showed a slightly weaker reactivity to three strains than strain O35E. Thus, the antibodies elicited by immunization of CD protein isolated from strain O35E cross-reacted with all heterologous strains tested.

For vaccine development, CD specific amino acid sequences may be purified from B. catarrhalis or may be purified from a host containing a recombinant vector which expresses CD or CD peptides. Such hosts include, but are not limited to, bacterial transformants, yeast transformants, filamentous fungal transformants, and cultured cells that have been either infected or transfected with a vector which encodes CD amino acid sequences. Peptides or oligopeptides corresponding to portions of the CD protein may be produced from chemical or enzymatic cleavage of CD protein (See for example, Embodiment D); or chemically synthesized using methods known in the art and with the amino acid sequence deduced from the nucleotide sequence of the gene encoding CD as a reference. Alternatively, CD peptides may be produced from a recombinant vector (See for example, Embodiment A). The protein, peptide, or oligopeptide immunogen is included as the relevant immunogenic material in the vaccine formulation, and in therapeutically effective amounts, to induce an immune response. Many methods are known for the introduction of a vaccine formulation into the human or animal to be vaccinated. These include, but are not limited to, intradermal, intramuscular, intraperitoneal, intravenous, subcutaneous, ocular, intranasal, and oral administration. The vaccine may further comprise a physiological carrier such as a solution, a polymer or liposomes; and an adjuvant, or a combination thereof.

Various adjuvants are used in conjunction with vaccine formulations. The adjuvants aid by modulating the immune response and in attaining a more durable and higher level of immunity using smaller amounts of vaccine antigen or fewer doses than if the vaccine antigen were administered alone. Examples of adjuvants include incomplete Freund's adjuvant, Adjuvant 65 (containing peanut oil, mannide monooleate and aluminum monostearate), oil emulsions, Ribi adjuvant, the pluronic polyols, polyamines, Avridine, Quil A, saponin, MPL, QS-21, and mineral gels such as aluminum hydroxide, aluminum phosphate, etc.

Another embodiment of this mode of the invention involves the production of CD-specific amino acid sequences as a hapten, i.e. a molecule which cannot by itself elicit an immune response. In such case, the hapten may be covalently bound to a carrier or other immunogenic molecule which will confer immunogenicity to the coupled hapten when exposed to the immune system. Thus, such a CD-specific hapten liked to a carrier molecule may be the immunogen in a vaccine formulation.

Another mode of this embodiment provides for either a live recombinant viral vaccine, recombinant bacterial vaccine, recombinant attenuated bacterial vaccine, or an inactivated recombinant viral vaccine which is used to protect against infections caused by B. catarrhalis. Vaccinia virus is the best known example, in the art, of an infectious virus that is engineered to express vaccine antigens derived from other organisms. The recombinant live vaccinia virus, which is attenuated or otherwise treated so that it does not cause disease by itself, is used to immunize the host. Subsequent replication of the recombinant virus within the host provides a continual stimulation of the immune system with the vaccine antigens such as CD protein, or CD peptides, thereby providing long-lasting immunity.

Other live vaccine vectors include: adenovirus, cytomegalovirus, and preferably the poxviruses such as vaccinia (Paoletti and Panicali, U.S. Pat. No. 4,603,112) and attenuated Salmonella strains (Stocker et al., U.S. Pat. Nos. 5,210,035; 4,837,151; and 4,735,801; and Curriss et al., 1988, Vaccine 6:155–160). Live vaccines are particularly advantageous because they continually stimulate the immune system which can confer substantially long-lasting immunity. When the immune response is protective against subsequent B. catarrhalis infection, the live vaccine itself may be used in a preventative vaccine against B. catarrhalis.

To illustrate this mode of the embodiment, using molecular biological techniques such as those illustrated in Embodiment A, the gene encoding CD, or a gene fragment encoding one or more CD peptides may be inserted into the vaccinia virus genomic DNA at a site which allows for expression of CD epitopes but does not negatively affect the growth or replication of the vaccinia virus vector. The resultant recombinant virus can be used as the immunogen in a vaccine formulation. The same methods can be used to construct an inactivated recombinant viral vaccine formulation except that the recombinant virus is inactivated, such as by chemical means known in the art, prior to use as an immunogen and without substantially affecting the immunogenicity of the expressed immunogen. A mixture of inactivated viruses which express different epitopes may be used in the formulation of a multivalent inactivated vaccine. In either case, the inactivated recombinant vaccine or mixture of inactivated viruses may be formulated with a suitable adjuvant in order to enhance the immunological response to the vaccine antigens.

In another variation of this embodiment, genetic material is used directly as the vaccine formulation. Nucleic acid (DNA or RNA) containing sequences encoding CD protein, CD peptide or CD oligopeptide, operatively linked to one or more regulatory elements can be introduced directly to vaccinate the individual ("direct gene transfer") against pathogenic strains of *B. catarrahlis*. Direct gene transfer into a vaccinated individual, resulting in expression of the genetic material by the vaccinated individual's cells such as vascular endothelial cells as well as the tissue of the major organs, has been demonstrated by techniques in the art such as by injecting intravenously an expression plasmid:cationic liposome complex (Zhu et al., 1993, Science 261:209–211). Other effective methods for delivering vector DNA into a target cell are known in the art. In one example, purified recombinant plasmid DNA containing viral genes has been used to inoculate (whether parentally, mucosally, or via gene-gun immunization) vaccinees to induce a protective immune response (Fynan et al., 1993, Proc. Natl. Acad. Sci. U.S.A. 90:11478–11482). In another example, cells removed from an individual can be transfected or electroporated by standard procedures known in the art, resulting in the introduction of the recombinant vector DNA into the target cell. Cells containing the recombinant vector DNA may then be selected for using methods known in the art such as via a selection marker expressed in the vector, and the selected cells may then be re-introduced into the individual to express CD protein, CD peptide, or CD oligopeptide.

One preferred method of vaccination with genetic material comprises the step of administering to the individual the nucleic acid molecule that comprises a nucleic acid sequence that encodes for one or more of the CD protein, CD peptides, or CD oligopeptides, wherein the nucleic acid molecule is operatively linked to one or more regulatory sequences necessary for expression. The nucleic acid molecule can be administered directly, or first introduced into a viral vector and administered via the vector. The nucleic acid molecule can be administered in a pharmaceutically acceptable carrier or diluent and may contain compounds that can enhance the effectiveness of the vaccine. These additional compounds include, but are not limited to, adjuvants that enhance the immune response, and compounds that are directed to modulate the immune response, e.g. cytokines, collectively referred to as "immune modulators"; or other compounds which increase the uptake of nucleic acid by the cells, referred to as "nucleic acid uptake enhancers". The immunization with the nucleic acid molecule can be through any parental route (intravenous, intraperitoneal, intradermal, subcutaneous, or intramuscular), or via contact with mucosal surfaces of the nasopharynx, trachea, or gastrointestinal tract.

As an alternative to active immunization, such as where an immunocompromised individual is suffering from a potentially life-threatening infection caused by *B. catarrhalis*, immunization may be passive, i.e. immunization comprising administration of purified human immunoglobulin containing antibody against CD epitopes.

It should be understood that while the invention has been described in detail herein, the examples were for illustrative purposes only. Other modifications of the embodiments of the present invention that are obvious to those skilled in the art of molecular biology, medical diagnostics, and related disciplines are intended to be within the scope of the appended claims.

What is claimed is:

1. A recombinant vector comprising a DNA sequence encoding one or more antigenic epitopes of CD, wherein CD is an outer membrane protein of *Branhamella catarrhalis* having an apparent molecular mass determined by polyacrylamide gel electrophoresis of about 55,000 to 60,000 daltons and comprises an amino acid sequence shown in SEQ ID NO. 14.

2. The recombinant vector according to claim 1, wherein CD comprises an amino acid sequence of SEQ ID NO. 14 from amino acid residues 1 to 427.

3. The recombinant vector according to claim 1, wherein CD comprises an amino acid sequence of SEQ ID NO. 14 from amino acid residues −26 to 427.

4. The recombinant vector of claim 1, wherein the vector is selected from the group consisting of a plasmid vector, phagemid vector, cosmid vector, and a viral vector.

5. An isolated nucleic acid molecule selected from the group consisting of a gene depicted as a 1359 base pair open reading frame of SEQ ID No. 14, and a fragment of said gene, wherein said fragment encodes at least one epitope of outer membrane protein CD, wherein CD is an outer membrane protein of *Branhamella catarrhalis* having an apparent molecular mass of about 55,000 to 60,000 daltons determined by polyacrylamide gel electrophoresis and comprises an amino acid sequence shown in SEQ ID No. 14.

6. A recombinant microorganism containing the nucleic acid molecule of claim 5, and expresses a CD amino acid sequence selected from the group consisting of CD protein, CD peptides and CD oligopeptides, wherein CD is an outer membrane protein of *Branhamella catarrhalis* having an apparent molecular mass of about 55,000 to 60,000 daltons determined by polyacrylamide gel electrophoresis and comprises an amino acid sequence shown in SEQ ID NO. 14.

7. A microorganism of claim 6, which is a vaccinia virus, adenovirus, or cytomegalovirus.

8. A microorganism of claim 6, which is a bacterium of the genus *Salmonella*.

9. A method for producing a purified peptide, oligopeptide or protein having one or more antigenic epitopes of CD, wherein CD is an outer membrane protein of *Branhamella catarrhalis* comprising an amino acid sequence of SEQ ID NO.14, said method comprises (a) growing in culture the recombinant microorganism according to claim 6; and (b) isolating said peptide, oligopeptide, or protein having one or more antigenic epitopes of CD from the cultured recombinant microorganism or from medium used for culture.

* * * * *